US009827404B2

United States Patent
Nance et al.

(10) Patent No.: US 9,827,404 B2
(45) Date of Patent: Nov. 28, 2017

(54) EXPANDABLE TRANS-SEPTAL SHEATH

(71) Applicant: Onset Medical Corporation, Irvine, CA (US)

(72) Inventors: Edward J. Nance, Corona, CA (US); Jay Lenker, Laguna Beach, CA (US); George F. Kick, Casa Grande, AZ (US); Hyun T. Nguyen, Santa Ana, CA (US)

(73) Assignee: Onset Medical Corporation, Irvine, CA (US)

( * ) Notice: Subject to any disclaimer, the term of this patent is extended or adjusted under 35 U.S.C. 154(b) by 624 days.

(21) Appl. No.: 13/678,422

(22) Filed: Nov. 15, 2012

(65) Prior Publication Data
US 2013/0281978 A1 Oct. 24, 2013

Related U.S. Application Data

(62) Division of application No. 11/958,885, filed on Dec. 18, 2007, now Pat. No. 8,337,518.
(Continued)

(51) Int. Cl.
*A61M 29/00* (2006.01)
*A61M 29/02* (2006.01)
(Continued)

(52) U.S. Cl.
CPC ....... *A61M 29/02* (2013.01); *A61B 17/12022* (2013.01); *A61B 17/12122* (2013.01);
(Continued)

(58) Field of Classification Search
CPC ............ A61B 17/3423; A61B 17/3431; A61B 17/3439; A61B 2017/3433;
(Continued)

(56) References Cited

U.S. PATENT DOCUMENTS 668,879 A 2/1901 Miller
1,213,001 A 1/1917 Philips
(Continued)

FOREIGN PATENT DOCUMENTS

EP 177177 A2 4/1986
EP 0249456 A2 12/1987
(Continued)

OTHER PUBLICATIONS

International Search Report for Application No. PCT/US2009/044031 dated Dec. 22, 2009 (the PCT counterpart of U.S. Appl. No. 12/258,233).
(Continued)

*Primary Examiner* — Katherine Rodjom
(74) *Attorney, Agent, or Firm* — Inskeep IP Group, Inc.

(57) ABSTRACT

Disclosed is an expandable transluminal sheath, for introduction into the body while in a first, low cross-sectional area configuration, and subsequent expansion of at least a part of the distal end of the sheath to a second, enlarged cross-sectional configuration. The sheath is configured for use in the vascular system and has utility in the performance of procedures in the left atrium. The access route is through the inferior vena cava to the right atrium, where a transseptal puncture, followed by advancement of the catheter is completed. The distal end of the sheath is maintained in the first, low cross-sectional configuration during advancement to the right atrium and through the atrial septum into the left atrium. The distal end of the sheath is subsequently expanded using a radial dilatation device.

13 Claims, 22 Drawing Sheets

Related U.S. Application Data

(60) Provisional application No. 60/871,091, filed on Dec. 20, 2006.

(51) Int. Cl.
*A61B 17/12* (2006.01)
*A61B 17/34* (2006.01)
*A61B 18/14* (2006.01)
*A61B 17/00* (2006.01)
*A61B 18/00* (2006.01)
*A61M 25/00* (2006.01)
*A61M 25/10* (2013.01)

(52) U.S. Cl.
CPC .... *A61B 17/12159* (2013.01); *A61B 17/3468* (2013.01); *A61B 17/3423* (2013.01); *A61B 18/1492* (2013.01); *A61B 2017/00243* (2013.01); *A61B 2017/00278* (2013.01); *A61B 2017/00292* (2013.01); *A61B 2017/00575* (2013.01); *A61B 2017/00592* (2013.01); *A61B 2017/00632* (2013.01); *A61B 2017/1205* (2013.01); *A61B 2017/3486* (2013.01); *A61B 2018/00351* (2013.01); *A61B 2018/1407* (2013.01); *A61M 25/0045* (2013.01); *A61M 25/0053* (2013.01); *A61M 25/1011* (2013.01)

(58) Field of Classification Search
CPC .. A61B 2017/3445; A61B 2017/00243; A61B 2017/00292; A61M 39/10; A61M 2039/1016; A61M 2039/1027; A61M 2039/1044
See application file for complete search history.

(56) References Cited

U.S. PATENT DOCUMENTS

| | | |
|---|---|---|
| 1,248,492 A | 12/1917 | Hill |
| 2,548,602 A | 4/1948 | Greenburg |
| 3,509,883 A | 11/1967 | Dibelius |
| 3,545,443 A | 12/1970 | Ansari |
| 3,742,958 A | 7/1973 | Rundles |
| 3,789,852 A | 2/1974 | Kim et al. |
| 3,874,388 A | 4/1975 | King et al. |
| 3,902,492 A | 9/1975 | Greenhalgh |
| 4,018,230 A | 4/1977 | Ochiai et al. |
| 4,141,364 A | 2/1979 | Schultze |
| 4,338,942 A | 7/1982 | Fogarty |
| 4,401,433 A | 8/1983 | Luther |
| 4,411,655 A | 10/1983 | Schreck |
| 4,451,256 A | 5/1984 | Weikl et al. |
| 4,479,497 A | 10/1984 | Fogarty et al. |
| 4,581,025 A | 4/1986 | Timmermans |
| 4,589,868 A | 5/1986 | Dretler |
| 4,601,713 A | 7/1986 | Fuqua |
| 4,610,668 A | 9/1986 | Silvestrini et al. |
| 4,650,466 A | 3/1987 | Luther |
| 4,710,181 A | 12/1987 | Fuqua |
| 4,716,901 A | 1/1988 | Jackson et al. |
| 4,738,666 A | 4/1988 | Fuqua |
| 4,739,762 A | 4/1988 | Palmaz |
| 4,753,221 A | 6/1988 | Kensey et al. |
| 4,772,266 A | 9/1988 | Groshong |
| 4,790,817 A | 12/1988 | Luther |
| 4,798,193 A | 1/1989 | Giesy et al. |
| 4,846,791 A | 7/1989 | Hattler et al. |
| 4,865,593 A | 9/1989 | Ogawa et al. |
| 4,869,717 A | 9/1989 | Adair |
| 4,888,000 A | 12/1989 | McQuilkin et al. |
| 4,896,669 A | 1/1990 | Bhate et al. |
| 4,899,729 A | 2/1990 | Gill et al. |
| 4,919,647 A | 4/1990 | Nash |
| 4,921,479 A | 5/1990 | Grayzel |
| 4,954,126 A | 9/1990 | Wallsten |
| 4,955,895 A | 9/1990 | Sugiyama et al. |
| 4,972,827 A | 11/1990 | Kishi et al. |
| 4,986,830 A | 1/1991 | Owens et al. |
| 5,011,488 A | 4/1991 | Ginsburg et al. |
| 5,045,056 A | 9/1991 | Behl |
| 5,059,183 A | 10/1991 | Semrad |
| 5,078,736 A | 1/1992 | Behl |
| 5,092,839 A | 3/1992 | Kipperman |
| 5,100,388 A | 3/1992 | Behl et al. |
| 5,108,413 A | 4/1992 | Moyers |
| 5,112,304 A | 5/1992 | Barlow et al. |
| 5,112,308 A | 5/1992 | Olsen et al. |
| 5,116,318 A | 5/1992 | Hillstead |
| 5,122,122 A | 6/1992 | Allgood |
| 5,139,511 A | 8/1992 | Gill et al. |
| 5,158,545 A | 10/1992 | Trudell et al. |
| 5,176,659 A | 1/1993 | Mancini |
| 5,183,464 A | 2/1993 | Dubrul et al. |
| 5,188,602 A | 2/1993 | Nichols |
| 5,190,528 A | 3/1993 | Fonger et al. |
| 5,201,756 A | 4/1993 | Horzewski et al. |
| 5,201,901 A | 4/1993 | Harada et al. |
| 5,213,376 A * | 5/1993 | Szabo ............... F16L 37/084 285/39 |
| 5,222,938 A | 6/1993 | Behl |
| 5,222,971 A | 6/1993 | Willard et al. |
| 5,224,935 A | 7/1993 | Hollands |
| 5,234,425 A | 8/1993 | Fogarty et al. |
| 5,250,025 A | 10/1993 | Sosnowski et al. |
| 5,250,033 A | 10/1993 | Evans et al. |
| 5,275,611 A | 1/1994 | Behl |
| 5,295,994 A | 3/1994 | Bonutti |
| 5,312,360 A | 5/1994 | Behl |
| 5,316,360 A | 5/1994 | Feikma |
| 5,318,588 A | 6/1994 | Horzewski et al. |
| 5,320,611 A | 6/1994 | Bonutti et al. |
| 5,324,261 A | 6/1994 | Amundson et al. |
| 5,346,503 A | 9/1994 | Chow et al. |
| 5,380,304 A | 1/1995 | Parker |
| 5,392,766 A | 2/1995 | Masterson et al. |
| 5,395,341 A | 3/1995 | Slater |
| 5,395,349 A | 3/1995 | Quiachon et al. |
| 5,407,430 A | 4/1995 | Peters |
| 5,409,469 A | 4/1995 | Schaerf |
| 5,431,676 A | 7/1995 | Dubrul et al. |
| 5,433,708 A | 7/1995 | Nichols et al. |
| 5,454,790 A | 10/1995 | Dubrul |
| 5,458,574 A | 10/1995 | Machold et al. |
| 5,460,170 A | 10/1995 | Hammerslag |
| 5,497,774 A * | 3/1996 | Swartz et al. ............... 600/585 |
| 5,514,091 A | 5/1996 | Yoon |
| 5,514,236 A | 5/1996 | Avellanet et al. |
| 5,527,336 A | 6/1996 | Rosenbluth |
| 5,540,658 A | 7/1996 | Evans et al. |
| 5,542,928 A | 8/1996 | Evans et al. |
| 5,662,614 A | 9/1997 | Edoga |
| 5,662,700 A | 9/1997 | Lazarus |
| 5,674,857 A | 10/1997 | Anderson et al. |
| 5,676,693 A | 10/1997 | LaFontaine |
| 5,700,253 A | 12/1997 | Parker |
| 5,713,867 A | 2/1998 | Morris |
| 5,738,667 A | 4/1998 | Solar |
| 5,766,151 A | 6/1998 | Valley et al. |
| 5,766,203 A * | 6/1998 | Imran ............... A61F 2/958 604/103.05 |
| 5,776,141 A | 7/1998 | Klein et al. |
| 5,807,311 A | 9/1998 | Palestrant |
| 5,814,016 A | 9/1998 | Valley et al. |
| 5,846,251 A | 12/1998 | Hart |
| 5,863,366 A | 1/1999 | Snow |
| 5,868,702 A | 2/1999 | Stevens et al. |
| 5,885,217 A | 3/1999 | Gisselberg et al. |
| 5,885,238 A | 3/1999 | Stevens et al. |
| 5,888,196 A | 3/1999 | Bonutti |
| 5,908,448 A | 6/1999 | Roberts et al. |
| 5,911,702 A | 6/1999 | Romley et al. |
| 5,916,145 A | 7/1999 | Chu et al. |
| 5,928,181 A | 7/1999 | Coleman et al. |
| 5,964,730 A | 10/1999 | Williams et al. |

(56) References Cited

U.S. PATENT DOCUMENTS

| | | | |
|---|---|---|---|
| 5,971,938 A | 10/1999 | Hart et al. | |
| 5,997,508 A | 12/1999 | Lunn et al. | |
| 6,080,174 A | 6/2000 | Dubrul et al. | |
| 6,090,072 A | 7/2000 | Kratoska et al. | |
| 6,090,096 A | 7/2000 | St Goar et al. | |
| 6,120,480 A | 9/2000 | Zhang et al. | |
| 6,120,494 A | 9/2000 | Jonkman | |
| 6,123,689 A | 9/2000 | To et al. | |
| 6,129,707 A | 10/2000 | Cryer | |
| 6,139,517 A | 10/2000 | Macoviak et al. | |
| 6,149,578 A | 11/2000 | Downey et al. | |
| 6,152,141 A | 11/2000 | Stevens et al. | |
| 6,165,168 A * | 12/2000 | Russo | A61M 39/045 604/247 |
| 6,168,579 B1 | 1/2001 | Tsugita | |
| 6,183,443 B1 | 2/2001 | Kratoska et al. | |
| 6,197,016 B1 | 3/2001 | Fourkas et al. | |
| 6,228,052 B1 | 5/2001 | Pohndorf | |
| 6,231,498 B1 | 5/2001 | Pfeiffer et al. | |
| 6,231,551 B1 | 5/2001 | Barbut et al. | |
| 6,234,995 B1 | 5/2001 | Peacock, III | |
| 6,254,563 B1 | 7/2001 | Macoviak et al. | |
| 6,293,909 B1 | 9/2001 | Chu et al. | |
| 6,312,443 B1 | 11/2001 | Stone | |
| 6,338,725 B1 | 1/2002 | Hermann et al. | |
| 6,346,092 B1 | 2/2002 | Leschinsky | |
| 6,358,238 B1 | 3/2002 | Sherry | |
| 6,368,345 B1 | 4/2002 | Dehdashtian et al. | |
| 6,375,675 B2 | 4/2002 | Dehdashtian et al. | |
| 6,447,540 B1 | 9/2002 | Fontaine et al. | |
| 6,451,053 B1 | 9/2002 | Dehdashtian et al. | |
| 6,471,684 B2 | 10/2002 | Dulak et al. | |
| 6,494,860 B2 | 12/2002 | Rocamora et al. | |
| 6,494,893 B2 | 12/2002 | Dubrul et al. | |
| 6,524,268 B2 | 2/2003 | Hayner et al. | |
| 6,530,894 B1 | 3/2003 | Barbut | |
| 6,530,902 B1 | 3/2003 | Jonkman | |
| 6,533,770 B1 | 3/2003 | Lepulu et al. | |
| 6,537,247 B2 | 3/2003 | Shannon | |
| 6,547,760 B1 | 4/2003 | Samson et al. | |
| 6,565,552 B1 | 5/2003 | Barbut | |
| 6,576,007 B2 | 6/2003 | Dehdashtian et al. | |
| 6,579,259 B2 | 6/2003 | Stevens et al. | |
| 6,582,388 B1 | 6/2003 | Coleman et al. | |
| 6,582,395 B1 | 6/2003 | Burkett et al. | |
| 6,592,557 B2 | 7/2003 | Barbut | |
| 6,613,062 B1 | 9/2003 | Leckrone et al. | |
| 6,616,678 B2 | 9/2003 | Nishtala et al. | |
| 6,626,899 B2 | 9/2003 | Houser et al. | |
| 6,635,046 B1 | 10/2003 | Barbut | |
| 6,638,268 B2 | 10/2003 | Niazi | |
| 6,669,687 B1 | 12/2003 | Saadat | |
| 6,679,902 B1 | 1/2004 | Boyle et al. | |
| 6,692,462 B2 | 2/2004 | Mackenzie et al. | |
| 6,692,482 B2 | 2/2004 | Heller et al. | |
| 6,692,512 B2 | 2/2004 | Jang | |
| 6,695,810 B2 | 2/2004 | Peacock, III et al. | |
| 6,695,811 B2 | 2/2004 | Samson et al. | |
| 6,695,864 B2 | 2/2004 | Macoviak et al. | |
| 6,706,017 B1 | 3/2004 | Dulguerov | |
| 6,712,806 B2 | 3/2004 | St. Germain et al. | |
| 6,726,651 B1 | 4/2004 | Robinson et al. | |
| 6,743,196 B2 | 6/2004 | Barbut et al. | |
| 6,746,431 B2 | 6/2004 | Pfeiffer et al. | |
| 6,767,345 B2 | 7/2004 | St. Germain et al. | |
| 6,793,647 B1 | 9/2004 | Cryer | |
| 6,796,992 B2 | 9/2004 | Barbut | |
| 6,848,448 B1 | 2/2005 | St. Germain et al. | |
| 6,866,647 B2 | 3/2005 | Barbut | |
| 6,866,650 B2 | 3/2005 | Stevens et al. | |
| 6,872,223 B2 | 3/2005 | Roberts et al. | |
| 6,887,229 B1 | 5/2005 | Kurth | |
| 6,913,600 B2 | 7/2005 | Valley et al. | |
| 6,932,792 B1 | 8/2005 | St. Goar et al. | |
| 6,966,886 B2 | 11/2005 | Appling | |
| 7,011,645 B2 | 3/2006 | McGuckin, Jr. et al. | |
| 7,090,683 B2 * | 8/2006 | Brock et al. | 606/130 |
| 7,150,736 B2 | 12/2006 | Barbut et al. | |
| 7,229,403 B2 | 6/2007 | Schock et al. | |
| 7,309,334 B2 | 12/2007 | Von Hoffmann | |
| 7,699,864 B2 | 4/2010 | Kick et al. | |
| 7,713,193 B2 | 5/2010 | Nance et al. | |
| 7,722,568 B2 | 5/2010 | Lenker et al. | |
| 7,780,692 B2 | 8/2010 | Nance et al. | |
| 7,892,203 B2 | 2/2011 | Lenker et al. | |
| 7,951,110 B2 | 5/2011 | Bishop et al. | |
| 8,092,481 B2 | 1/2012 | Nance et al. | |
| 8,231,600 B2 | 7/2012 | Von Hoffman | |
| 8,282,664 B2 | 10/2012 | Nance et al. | |
| 8,337,518 B2 | 12/2012 | Nance et al. | |
| 8,348,892 B2 | 1/2013 | Lenker et al. | |
| 8,900,214 B2 * | 12/2014 | Nance et al. | 604/509 |
| 2001/0012950 A1 | 8/2001 | Nishtala et al. | |
| 2001/0037126 A1 | 11/2001 | Stack et al. | |
| 2002/0009535 A1 | 1/2002 | Michal et al. | |
| 2002/0010476 A1 | 1/2002 | Mulholland et al. | |
| 2002/0077653 A1 | 6/2002 | Hudson et al. | |
| 2002/0096183 A1 | 7/2002 | Stevens et al. | |
| 2002/0099431 A1 | 7/2002 | Armstrong et al. | |
| 2002/0169377 A1* | 11/2002 | Khairkhahan | A61B 17/32037 600/433 |
| 2003/0050600 A1 | 3/2003 | Ressemann et al. | |
| 2003/0135156 A1 | 7/2003 | Bencini et al. | |
| 2003/0212384 A1* | 11/2003 | Hayden | 604/533 |
| 2004/0006344 A1 | 1/2004 | Nguyen et al. | |
| 2004/0045645 A1 | 3/2004 | Zhou | |
| 2005/0085842 A1 | 4/2005 | Eversull et al. | |
| 2005/0124937 A1 | 6/2005 | Kick et al. | |
| 2005/0149105 A1 | 7/2005 | Leeflang et al. | |
| 2005/0209627 A1 | 9/2005 | Kick et al. | |
| 2005/0222576 A1 | 10/2005 | Kick et al. | |
| 2005/0251094 A1 | 11/2005 | Peterson | |
| 2006/0041270 A1 | 2/2006 | Lenker et al. | |
| 2006/0074476 A1 | 4/2006 | Holman et al. | |
| 2006/0125962 A1 | 6/2006 | Shelton et al. | |
| 2006/0135962 A1* | 6/2006 | Kick et al. | 606/108 |
| 2006/0135963 A1 | 6/2006 | Kick et al. | |
| 2006/0135981 A1 | 6/2006 | Lenker et al. | |
| 2006/0253102 A1 | 11/2006 | Nance et al. | |
| 2006/0259061 A1 | 11/2006 | Kick et al. | |
| 2007/0021648 A1 | 1/2007 | Lenker et al. | |
| 2007/0135793 A1 | 6/2007 | Barbut et al. | |
| 2007/0239170 A1 | 10/2007 | Brock et al. | |
| 2008/0082079 A1 | 4/2008 | Braga et al. | |
| 2008/0200943 A1 | 8/2008 | Barker et al. | |
| 2008/0243081 A1 | 10/2008 | Nance et al. | |
| 2009/0287182 A1 | 11/2009 | Bishop et al. | |
| 2009/0287183 A1 | 11/2009 | Bishop et al. | |
| 2010/0228077 A1 | 9/2010 | Lenker et al. | |
| 2011/0112567 A1 | 5/2011 | Lenker et al. | |
| 2011/0144690 A1 | 6/2011 | Bishop et al. | |
| 2011/0152763 A1 | 6/2011 | Bishop et al. | |
| 2011/0282156 A1 | 11/2011 | Lenker et al. | |
| 2012/0041466 A1 | 2/2012 | Bishop et al. | |
| 2012/0283633 A1 | 11/2012 | Von Hoffman | |

FOREIGN PATENT DOCUMENTS

| | | |
|---|---|---|
| EP | 0385920 A2 | 9/1990 |
| EP | 0206553 | 1/1991 |
| EP | 0206553 B1 | 1/1991 |
| EP | 0421650 A1 | 4/1991 |
| EP | 0546766 A2 | 6/1993 |
| JP | 9-501594 A | 2/1997 |
| JP | 10-505767 A | 6/1998 |
| JP | 2003-530190 A | 10/2003 |
| WO | WO1992/019312 A1 | 11/1992 |
| WO | WO1995/005207 A2 | 2/1995 |
| WO | WO1995/030374 A1 | 11/1995 |
| WO | WO1996/008286 A1 | 3/1996 |
| WO | WO1999/016499 A1 | 4/1999 |
| WO | WO 1999/017665 | 4/1999 |
| WO | WO1999/017665 A1 | 4/1999 |
| WO | WO 2000/35527 | 6/2000 |

(56) References Cited

FOREIGN PATENT DOCUMENTS

| WO | WO2001/078596 A1 | 10/2001 |
|---|---|---|
| WO | WO2003/011154 A2 | 2/2003 |
| WO | WO2003/077733 A2 | 9/2003 |
| WO | WO 2003/090834 | 11/2003 |
| WO | WO2003/090834 A2 | 11/2003 |
| WO | WO 2006/029370 | 3/2006 |

OTHER PUBLICATIONS

International Search Report for Application No. PCT/US05/32291 dated Apr. 3, 2007 (the PCT counterpart of U.S. Appl. No. 11/222,498).

International Search Report for Application No. PCT/US2008/058771 dated Jul. 28, 2008 (the PCT counterpart of U.S. Appl. No. 12/058,455).

International Search Report and Written Opinion for Application No. PCT/US2007/088005 dated Jun. 10, 2008 (the PCT counterpart of the present application).

Extended Search Report dated Apr. 25, 2012 in European Patent Application No. 05796582.4, 5 pages.

International Search Report dated Apr. 3, 2007 in International Application No. PCT/US05/32291, 3 pages.

\* cited by examiner

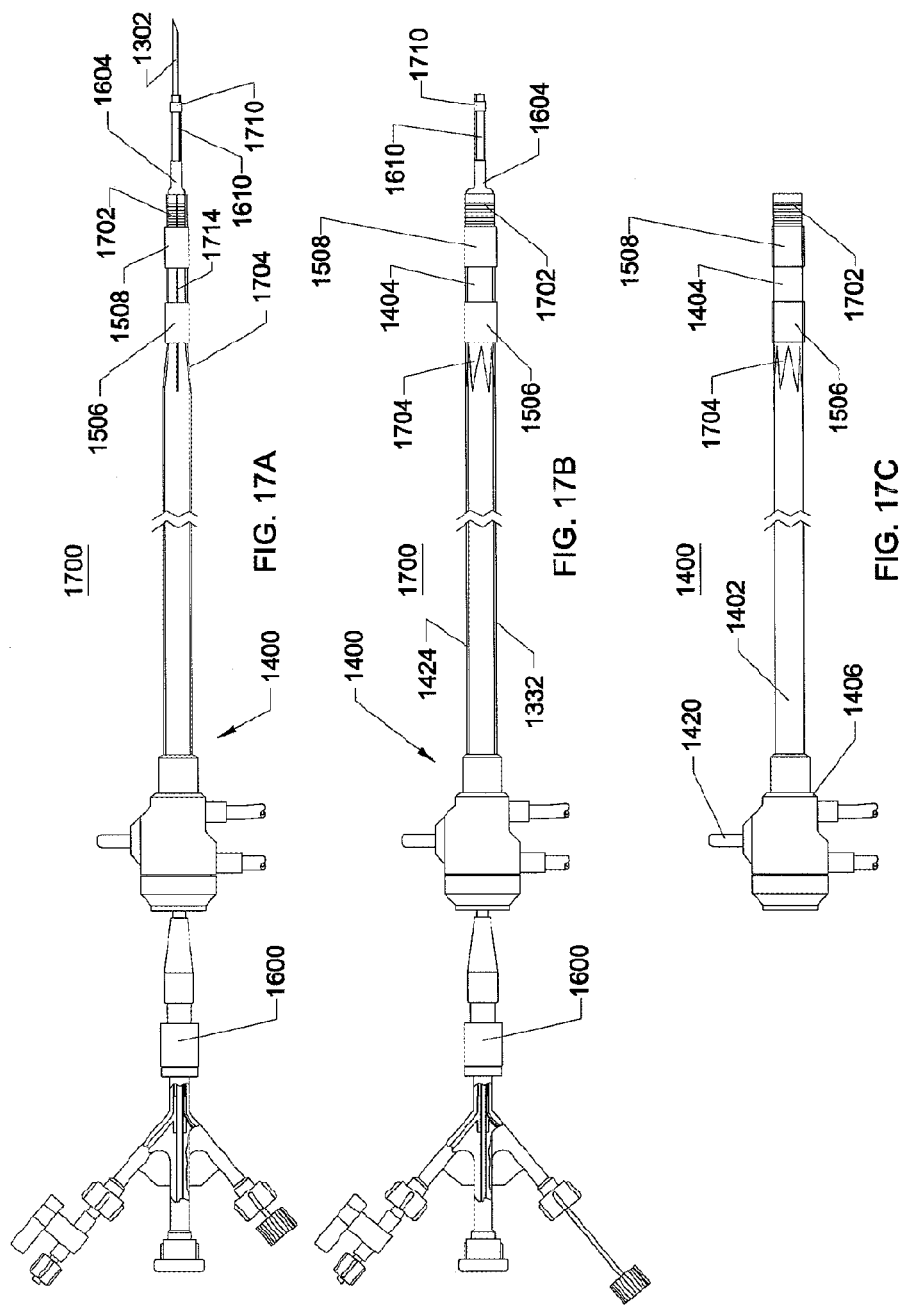

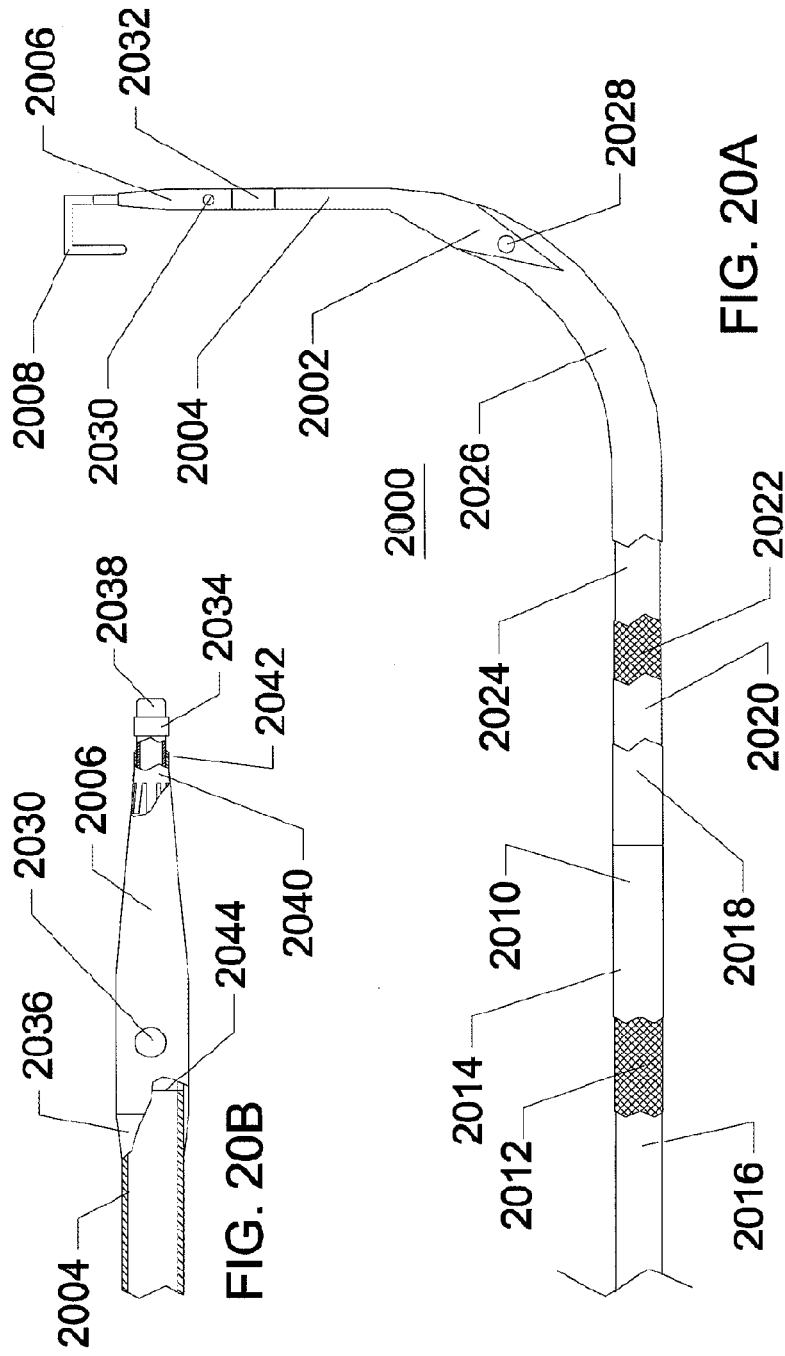

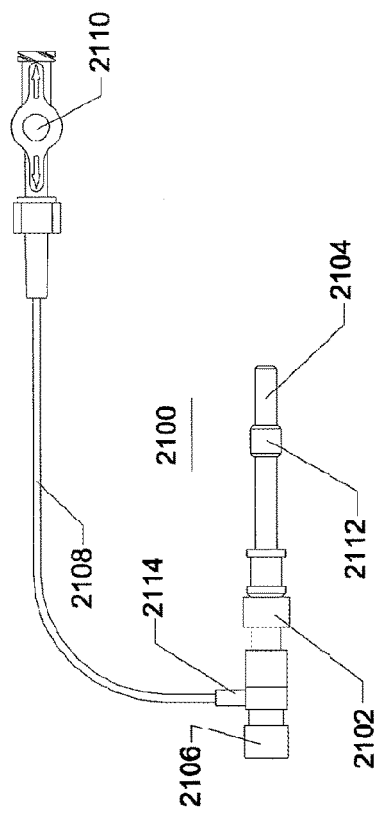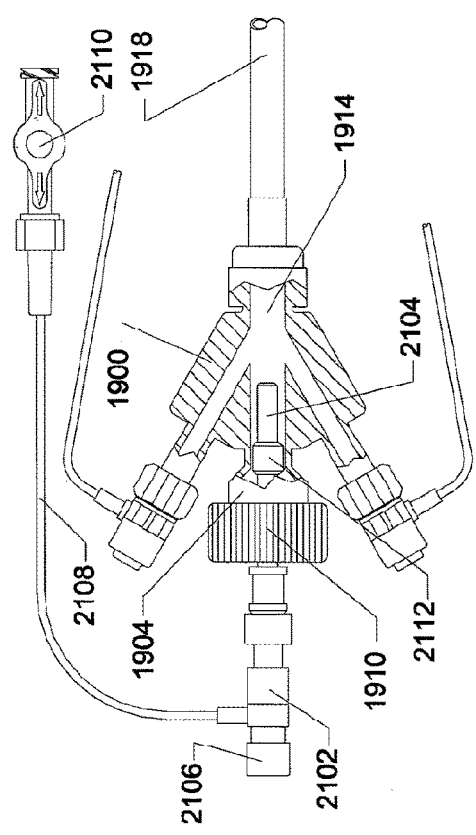
FIG. 21A
FIG. 21B

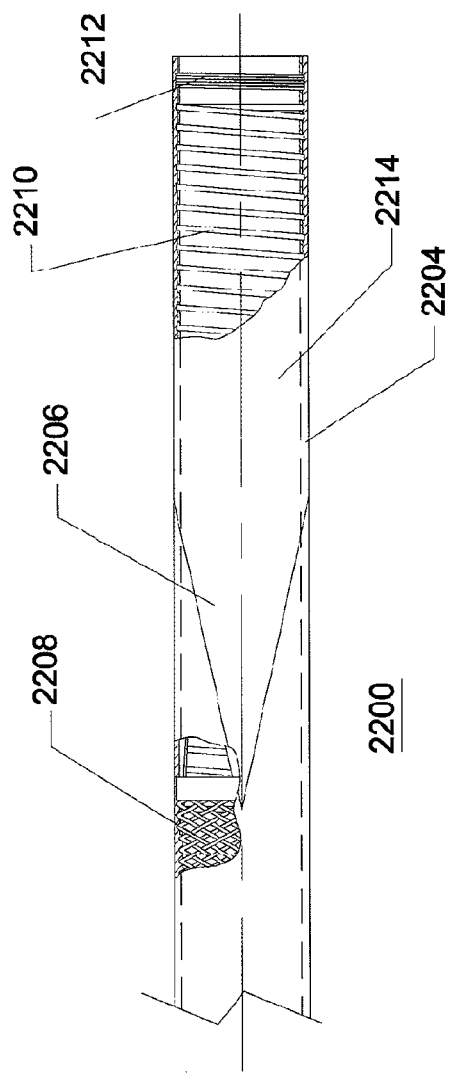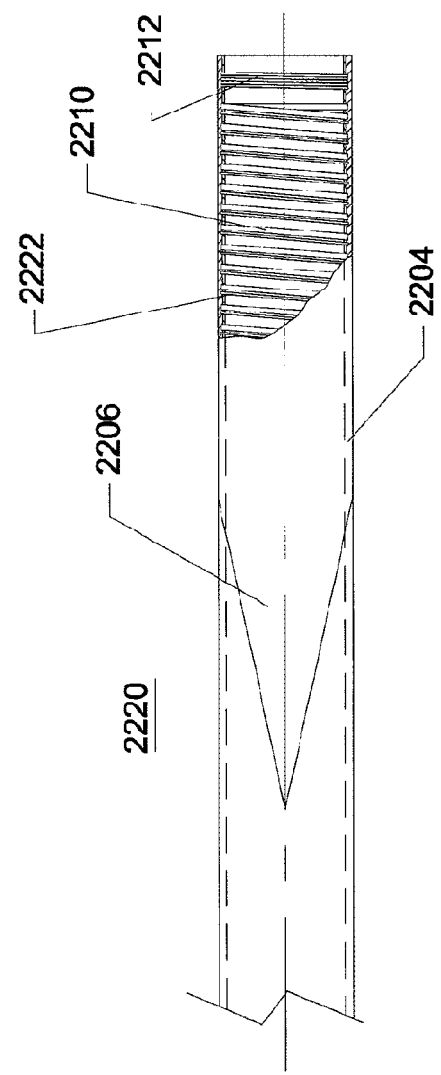

EXPANDABLE TRANS-SEPTAL SHEATH

CROSS-REFERENCE TO RELATED APPLICATIONS

This application is a divisional of U.S. patent application Ser. No. 11/958,885, filed Dec. 18, 2007, the entire contents of which are hereby incorporated by reference herein, and which claims the priority benefit of U.S. Provisional Application No. 60/871,091 filed Dec. 20, 2006, the entire contents of which are hereby incorporated by reference herein.

BACKGROUND OF THE INVENTION

Field of the Invention

The invention relates to medical devices for percutaneously accessing body lumens and cavities and, more particularly, to methods and devices for accessing the cardiovascular system.

Description of the Related Art

A wide variety of diagnostic or therapeutic procedures involves the introduction of a device into the vasculature through a percutaneous incision at an access site. Such regions of the vasculature, preferred for access, include both the arteries and veins, typically at peripheral locations in the body. Typical access sites include the jugular vein, the subclavian artery, the subclavian vein, the brachial artery and vein, the femoral arteries and the femoral veins. Techniques commonly known for such vascular access include the Seldinger technique. The Seldinger technique involves using a hollow needle to puncture the skin and gain access to the selected artery or vein. A guidewire is next placed through the hollow needle into the selected region of vasculature. The guidewire may be advanced to a target location in the vasculature, often more than 100 cm away from the access site. The needle is removed and a tapered dilator with a sheath and a central lumen in the dilator is advanced over the guidewire into the vasculature. The dilator is next removed and a guide catheter is advanced through the sheath over the guidewire. The guide catheter can be advanced all the way, or part way, to the target site. The guide catheter, following or without removal of the guidewire, can be used for directing therapeutic or diagnostic catheters to regions of the vasculature and central circulation, including external and internal structures of the heart. A general objective of access systems, which have been developed for this purpose, is to minimize the cross-sectional area of the access lumen, while maximizing the available space for the diagnostic or therapeutic catheter placement therethrough. These procedures are especially suited for coronary angioplasty, stent placement, cerebrovascular coil placement, prosthetic heart valve replacement, diagnostic cardiac catheterization, and the like.

Electrophysiology (EP) mapping and cardiac tissue ablation procedures are examples of diagnostic or therapeutic interventional procedures that are commonly performed on the heart. The procedure involves the steps of inserting a hollow needle into the femoral vein via a percutaneous puncture. A guidewire is next inserted through the central lumen of the needle into the femoral vein. The guidewire is routed, under fluoroscopic control, cranially toward the heart until it reaches the right atrium via the inferior vena cava. The hollow needle is removed and a sheath with a tapered tip central obturator further including a central guidewire lumen, termed a dilator, is routed over the guidewire, through the skin puncture, through the wall of the femoral vein, and into the central lumen of the femoral vein. The central obturator or dilator is next removed. A Mullins catheter is next routed through the sheath, over the guidewire, and advanced to the right atrium. The guidewire is removed and a Brockenbrough™ (Trademark of C. R. Bard, Inc.)-type needle is inserted through the proximal end of the Mullins™ catheter and routed to the right atrium. The Mullins catheter is positioned, under fluoroscopic guidance, so that its distal end is located in the Foramenal valley, a feature in the septal wall of myocardium that divides the right atrium from the left atrium. The Foramenal valley is the remains of a communication between the right and left atrium, which exists prior to birth, but which closes following birth due to the pressures imposed by the beating heart of the newborn infant. The Brockenbrough needle is next advanced through the atrial septum in the general region of the Foramenal valley. The Mullins catheter is next advanced over the Brockenbrough needle until its distal end resides within the left atrium. Hemostatic valves at the proximal end of all hollow devices permit sealing around catheters and devices inserted therethrough with corresponding prevention or minimization of blood loss and the entry of air.

The procedure continues with the Brockenbrough needle being withdrawn and replaced with a 0.032 to 0.038 inch diameter guidewire, generally of the stiff variety. This guidewire may have a bifurcated distal end to prevent inadvertent retraction once the guidewire has been advanced and expanded into the left atrium. The Mullins catheter is next withdrawn and replaced with a guide catheter having internal dimensions generally around 8 French and a tapered, removable obturator. The guide catheter is advanced into the right atrium and across the atrial septum, following which the obturator is removed. At this time, diagnostic and therapeutic catheters can be advanced into the left atrium so that appropriate EP mapping and ablation can occur. However, problems sometime arise, when trying to pass the guide catheter across the atrial septum, in that the tract generated by the Brockenbrough needle and Mullins catheter closes too tightly to allow passage of the guide catheter. At this point, a balloon catheter is advanced over the guidewire and through the guide catheter. The balloon catheter is advanced so that its dilatation balloon traverses the atrial septum. The balloon catheter is next inflated to stretch the tissues surrounding the atrial septal puncture. At this time, the guide catheter can have its dilator re-inserted and the entire assembly advanced over the guidewire through the atrial septum and into the left atrium.

Current therapeutic techniques may involve advancing an EP mapping catheter through the guide catheter and positioning the EP mapping catheter at various locations within the left atrium. Electrocardiogram signals are sensed by the EP mapping catheter. These signals are conducted or transmitted from the distal tip to the proximal end over electrical lines routed along the length of the EP catheter. The signals are analyzed by equipment electrically connected to the proximal end of the EP mapping catheter. Catheter guidance is generally accomplished using X-ray fluoroscopy, ultrasound imaging such as ICE, TEE, and the like. Therapy generally involves radio-frequency (RF) electromagnetic wave generation by external equipment electrically connected to an EP therapeutic catheter. The EP therapeutic catheter is advanced into the left atrium into regions of foci of electrical interference of the hearts normal electrical conduction. Application of such radio-frequency energy at the tip of the EP therapeutic catheter, which is brought into contact with the myocardium, causes tissue ablation and the elimination of the sources of these spurious signals or re-entry waveforms. A primary area targeted for RF tissue ablation is the area surrounding the origin of the pulmonary veins. Often a ring-type electrode is beneficial in performing this procedure. Such tissue ablation can be performed using RF energy to generate heat, but it can also be performed using microwaves, Ohmic heating, high-intensity focused ultrasound (HIFU), or even cryogenic cooling. The cryogenic cooling may have certain advantages relative to heating methodologies in that tissue damage is lessened. Although a single atrial septal puncture may be adequate for electrophysiological mapping of the left atrium, therapeutic systems, including RF ablation devices often require that two atrial septal punctures be performed. A risk of atrial septal punctures includes potentially perforating the aorta, a high-pressure outlet line, which resides quite close to the atrial septum.

Provision is generally made to deflect instrumentation through substantial angles, between 20 and 90 degrees, within the right atrium to gain access to the atrial septum from a catheter routed cranially within the inferior vena cava. To address this situation, the Brockenbrough needle, the Mullins catheter, or both devices, are substantially curved devices. Significant skill is required, on the part of the cardiologist or electrophysiologist to negotiate the path to the atrial septum and into the left atrium using a Brockenbrough needle and a Mullins catheter.

One of the primary issues that arise during electrophysiology procedures in the heart is the need to remove and replace multiple instruments multiple times, which is highly expensive and adds substantial time to the conduct of the procedure. A reduction in the number of catheter and guidewire passes and interchanges would reduce procedure time, reduce the risk of complications, improve patient outcomes, reduce procedural cost, and increase the number of cases that could be performed at a given catheterization lab. Current procedures involving multiple atrial septal penetrations would be reduced in frequency or become less time consuming and less risky if only a single atrial septal penetration was necessary. Additional benefit could be derived if larger catheters could be used, thus enabling the use of more sophisticated, powerful, and accurate instruments to improve patient outcomes. The limitations of current systems are accepted by physicians but the need for improved instrumentation is clear. Furthermore, placement of implants within the left atrium, such as the Atritech Watchman™ or the Microvena PLAATO™ would be facilitated if a larger working channel could be made available.

Further reading related to the diagnosis and treatment of atrial fibrillation (AF) includes Hocini, M, et al., Techniques for Curative Treatment of Atrial Fibrillation, J. Cardiovasc Electrophysiol, 15(12): 1467-1471, 2004 and Pappone, C and Santinelli, V, The Who, What, Why, and How-to Guide for Circumferential Pulmonary Vein Ablation, J. Cardiovasc Electrophysiol, 15(10): 1226-1230, 2004. Further reading on RF ablation includes Chandrakantan, A, and Greenberg, M, Radiofrequency Catheter Ablation, eMedicine, topic 2957 Oct. 28, 2004. Further reading regarding catheter approaches to treating pathologies of the left atrium include Ross, et al, Transseptal Left Atrial Puncture; New Technique for the Measurement of Left Atrial Pressure in Man, Am J. Cardiol, 653-655, May 1959 and Changsheng M, et al., Transseptal Approach, an Indispensable Complement to Retrograde Aortic Approach for Radiofrequency Catheter Ablation of Left-Sided Accessory Pathways, J. HK Coll Cardiol, 3: 107-111, 1995.

A need, therefore, remains for improved access technology, which allows a device to be percutaneously or surgically introduced, endovascularly advanced to the right atrium, and enabled to cross the atrial septum by way of a myocardial puncture and Dotter-style follow-through. The device would further permit dilation of the myocardial puncture in the region of the atrial septum so that the sheath could pass relatively large diameter instruments or catheters, or multiple catheters through the same puncture. Such large dilations of the tissues of the atrial septum need to be performed in such a way that the residual defect is minimized when the device is removed. It would be beneficial if a cardiologist or hospital did not need to inventory and use a range of catheter diameters. It would be far more useful if one catheter or introducer sheath diameter could fit the majority of patients or devices. Ideally, the catheter or sheath would be able to enter a vessel or body lumen with a diameter of 3 to 12 French or smaller, and be able to pass instruments through a central lumen that is 14 to 30 French. The sheath or catheter would be capable of gently dilating the atrial septum using radially outwardly directed force and of permitting the exchange of instrumentation therethrough without being removed from the body. The sheath or catheter would also be maximally visible under fluoroscopy and would be relatively inexpensive to manufacture. The sheath or catheter would be kink resistant, provide a stable or stiff platform for atrial septum penetration, and minimize abrasion and damage to instrumentation being passed therethrough. The sheath or catheter would further minimize the potential for injury to body lumen or cavity walls or surrounding structures. The sheath or catheter would further possess certain steering capabilities so that it could be negotiated through substantial curves or tortuosity and permit instrument movement within the sheath.

SUMMARY OF THE INVENTION

A transluminal, radially expanding access sheath is provided according to an embodiment of the present invention. In an exemplary application, the sheath is utilized to provide access for a diagnostic or therapeutic procedure such as electrophysiological mapping of the heart, radio-frequency ablation of left atrial tissue, placement of left atrial implants, mitral valve repair, or the like. In an embodiment, the radially expanding access sheath is used to provide access to the left atrium by way of a trans-septal puncture and advancement in the atrial septum dividing the right and left atriums. In an embodiment, the sheath can have an introduction outside diameter that ranges from 3 to 12 French with a preferred range of 5 to 10 French. The diameter of the sheath can be expandable to permit instruments ranging up to 30 French to pass therethrough, with a preferred range of between 3 and 20 French. The sheath can have a working length ranging between 40-cm and 200-cm with a preferred length of 75-cm to 150-cm. The ability to pass the traditional electrophysiology therapeutic and diagnostic catheters and instruments as well as larger, more innovative, instruments through a catheter introduced with a small outside diameter is derived from the ability to atraumatically expand the distal end of the catheter or sheath to create a larger through lumen to access the cardiac chambers. The ability to pass multiple catheters through a single sheath with a single septal penetration is inherently safer and less time-consuming than a multiple septal puncture procedure. The expandable distal end of the catheter can comprise between 5% and 95% of the overall working length of the catheter. The proximal end of the catheter is generally larger than the distal end to provide for pushability, torqueaqbility (preferably approximately 1:1 torqueability), steerability, control, and the ability to easily pass large diameter instruments therethrough. In an embodiment, the sheath can be routed to its destination over one or more already placed guidewires with a diameter ranging from 0.010 inches up to 0.040 inches and generally approximating 0.035 to 0.038 inches in diameter. An advantage of approaching the treatment site by the veins, instead of the arteries, is that the venous pressure is lower than that in the arterial system, thus reducing the potential for catastrophic hemorrhage during the procedure. Another advantage of the system is that the sheath and dilator assembly are flexible enough to track over a guidewire and be steered by either the guidewire or by a Brockenbrough needle, inserted through the central lumen of the dilator.

One embodiment of the invention comprises an endovascular access system for providing minimally invasive access to atrial structures of the mammalian heart. The system includes an access sheath comprising an axially elongate tubular body that defines a lumen extending from the proximal end to the distal end of the sheath. At least a portion of the distal end of the elongate tubular body is radially expandable from a first, smaller cross-sectional profile to a second, greater cross-sectional profile. In an embodiment, the first, smaller cross-sectional profile is created by making axially oriented folds in the sheath material. These folds may be located in only one circumferential position on the sheath, or there may be a plurality of such folds or longitudinally oriented crimps in the sheath. The folds or crimps may be made permanent or semi-permanent by heat-setting the structure, once folded. In an embodiment, a releasable or expandable jacket is carried by the access sheath to restrain at least a portion of the elongate tubular structure in the first, smaller cross-sectional profile during insertion and up to or during inflation of the distal region. In another embodiment, the jacket is removed prior to inserting the sheath into the patient. In an embodiment, the elongate tubular body is sufficiently pliable to allow the passage of objects having a maximum cross-sectional size larger than an inner diameter of the elongate tubular body in the second, greater cross-sectional profile. The adaptability to objects of larger dimension is accomplished by pliability or re-shaping of the cross-section to the larger dimension in one direction accompanied by a reduction in dimension in a lateral direction. The adaptability may also be generated through the use of malleable or elastomerically deformable sheath material. This re-shaping or non-round cross-section can be beneficial in passing two or more catheters through a single sheath with a minimum lateral cross-sectional area. In one embodiment, the sheath tube comprises a reinforcing layer embedded within a membrane layer fabricated from polymeric materials. In one embodiment, an inner and outer layer of the sheath tube are fabricated from different polymers. In one embodiment, length of the sheath is between 50 and 250 cm. In one embodiment, the inner lumen of the sheath ranges between 6 and 30 French when the distal region is fully expanded.

In another embodiment of the invention, a transluminal access sheath assembly for providing minimally invasive access comprises an elongate tubular member having a proximal end and a distal end and defining a working inner lumen. In this embodiment, the tubular member comprises a folded or creased sheath that can be expanded by a dilatation balloon. The dilatation balloon, if filled with fluids, preferably liquids and further preferably radiopaque liquids, at appropriate pressure, can generate the force to radially dilate or expand the sheath. The dilatation balloon is removable to permit subsequent instrument passage through the sheath. Longitudinal runners may be disposed within the sheath to serve as tracks for instrumentation, which further minimize friction while minimizing the risk of catching the instrument on the expandable plastic tubular member. Such longitudinal runners are preferably circumferentially affixed within the sheath so as not to shift out of alignment. In yet another embodiment, the longitudinal runners may be replaced by longitudinally oriented ridges and valleys, termed flutes. The flutes, or runners, can be oriented along the longitudinal axis of the sheath, or they can be oriented in a spiral, or rifled, fashion.

In each of the embodiments, the proximal end of the access assembly, apparatus, or device is preferably fabricated as a structure that is flexible, resistant to kinking, and further retains both column strength and torqueability. Such structures include tubes fabricated with coils or braided reinforcements and preferably comprise inner walls that prevent the reinforcing structures from protruding, poking through, or becoming exposed to the inner lumen of the access apparatus. Such proximal end configurations may be single lumen, or multi-lumen designs, with a main lumen suitable for instrument, guidewire, endoscope, or obturator passage and additional lumens being suitable for control and operational functions such as balloon inflation. Such proximal tube assemblies can be affixed to the proximal end of the distal expandable segments described heretofore. In an embodiment, the proximal end of the catheter includes an inner layer of thin polymeric material, an outer layer of polymeric material, and a central region comprising a coil, braid, stent, plurality of hoops, or other reinforcement. It is beneficial to create a bond between the outer and inner layers at a plurality of points, most preferably at the interstices or perforations in the reinforcement structure, which is generally fenestrated. Such bonding between the inner and outer layers causes a braided structure to lock in place. In another embodiment, the inner and outer layers are not fused or bonded together in at least some, or all, places. When similar materials are used for the inner and outer layers, the sheath structure can advantageously be fabricated by fusing of the inner and outer layer to create a uniform, non-layered structure surrounding the reinforcement. The polymeric materials used for the outer wall of the jacket are preferably elastomeric to maximize flexibility of the catheter. The polymeric materials used in the composite catheter inner wall may be the same materials as those used for the outer wall, or they may be different. In another embodiment, a composite tubular structure can be co-extruded by extruding a polymeric compound with a stent, braid, or coil structure embedded therein. The reinforcing structure is preferably fabricated from annealed metals, such as fully annealed stainless steel, titanium, or the like. In this embodiment, once expanded, the folds or crimps can be held open by the reinforcement structure embedded within the sheath, wherein the reinforcement structure is malleable but retains sufficient force to overcome any forces imparted by the sheath tubing.

In an embodiment of the invention, it is beneficial that the sheath comprise a radiopaque marker or markers. The radiopaque markers may be affixed to the non-expandable portion or they may be affixed to the expandable portion. Markers affixed to the radially expandable portion preferably do not restrain the sheath or catheter from radial expansion or collapse. Markers affixed to the non-expandable portion, such as the catheter shaft of a balloon dilator can be simple rings that are not radially expandable. Radiopaque markers include shapes fabricated from malleable material such as gold, platinum, tantalum, platinum iridium, and the like. Radiopacity can also be increased by vapor deposition coating or plating metal parts of the catheter with metals or alloys of gold, platinum, tantalum, platinum-iridium, and the like. Expandable markers may be fabricated as undulated or wavy rings, bendable wire wound circumferentially around the sheath, or other structures such as are found commonly on stents, grafts, stent-grafts, or catheters used for endovascular access in the body. Expandable radiopaque structures may also include disconnected or incomplete surround shapes affixed to the surface of a sleeve or other expandable shape. Non-expandable structures include circular rings or other structures that completely surround the catheter circumferentially and are strong enough to resist expansion. In another embodiment, the polymeric materials of the catheter or sheath may be loaded with radiopaque filler materials such as, but not limited to, bismuth salts, or barium salts, or the like, at percentages ranging from 1% to 50% by weight in order to increase radiopacity. The radiopaque markers allow the sheath to be guided and monitored using fluoroscopy.

In order to enable radial or circumferential expansive translation of the reinforcement, it may be beneficial not to completely bond the inner and outer layers together, thus allowing for some motion of the reinforcement in translation as well as the normal circumferential expansion. Regions of non-bonding may be created by selective bonding between the two layers or by creating non-bonding regions using a slip layer fabricated from polymers, ceramics or metals. Radial expansion capabilities are important because the proximal end needs to transition to the distal expansive end and, to minimize manufacturing costs, the same catheter may be employed at both the proximal and distal end, with the expansive distal end undergoing secondary operations to permit radial or diametric expansion.

In another embodiment, the distal end of the catheter is fabricated using an inner tubular layer, which is thin and lubricious. This inner layer is fabricated from materials such as, but not limited to, FEP, PTFE, polyamide, polyethylene, polypropylene, Pebax, Hytrel, and the like. The reinforcement layer comprises a coil, braid, stent, or plurality of expandable, foldable, or collapsible rings, which are generally malleable and maintain their shape once deformed. Preferred materials for fabricating the reinforcement layer include but are not limited to, stainless steel, tantalum, gold, platinum, platinum-iridium, titanium, nitinol, and the like. The materials are preferably fully annealed or, in the case of nitinol, fully martensitic. The outer layer is fabricated from materials such as, but not limited to, FEP, PTFE, polyamide, polyethylene, polypropylene, polyurethane, Pebax, Hytrel, and the like. The inner layer is fused or bonded to the outer layer through holes in the reinforcement layer to create a composite unitary structure. The structure is crimped radially inward to a reduced cross-sectional area. A balloon dilator is inserted into the structure before crimping or after an initial crimping and before a final sheath crimping. The balloon dilator is capable of forced radial, or diametric, expansion of the reinforcement layer, which provides sufficient strength necessary to overcome any forces imparted by the polymeric tubing, thus controlling the cross-sectional shape of the polymeric tubing. The dilator is also capable of overcoming any forces imparted by tissues, including atrial or even ventricular myocardial tissue, through which the sheath is inserted.

Another embodiment of the invention comprises a method of providing endovascular access to the left atrium. The method first comprises percutaneously placing a hollow needle into the femoral vein, inserting a guidewire through the hollow needle into the vein, withdrawing the needle, and inserting a sheath with a tapered obturator into the puncture site and into the vein over the guidewire. The guidewire is next withdrawn, as is the tapered obturator and a 0.032 to 0.038-inch stiff guidewire is advanced into the vein and to the level of the right atrium or superior vena cava (SVC) through the inferior vena cava (IVC). A radially expandable sheath is next advanced into the femoral vein and advanced past the right atrium into the superior vena cava over the guidewire. The guidewire is next withdrawn and replaced with a Brockenbrough-type needle, which is advanced through the guidewire lumen of the expandable sheath. The Brockenbrough needle comprises a curved or bent distal end that can be used as a steering mechanism for the expandable sheath. The expandable sheath, with Brockenbrough needle inserted therethrough, is withdrawn caudally, turned toward the medial direction, and the distal tip is positioned against the Foramen Ovale of the atrial septum with the Brockenbrough needle withdrawn just inside the tip of a sheath dilator, which is pre-inserted within the radially collapsed sheath. The Brockenbrough-type needle is advanced through the atrial septum into the left atrium while maintaining the expandable sheath in position against the septal wall, either by normal cardiac movement or by mechanical forward force on the Brockenbrough needle. The expandable sheath is next advanced axially through the septal wall, over the Brockenbrough-type needle and the needle, affixed to its control wire is withdrawn from the proximal end of the expandable sheath. The dilator, positioned within the expandable sheath is next radially expanded causing the distal end of the sheath to expand radially so as to dilate the hole in the tissues of the atrial septum. The dilator is, next, deflated and removed form the sheath, leaving a large central lumen for the passage of instruments into the left atrium. The expanded sheath is capable of holding a single instrument or multiple instruments of, for example, 8 to 10 French diameter. Suitable hemostatic and anti-reflux valves and seals are affixed the distal end of all devices except guidewires to ensure maintenance of hemostasis and prevention of air entry into the vasculature. Following therapeutic or diagnostic procedures, or both, the sheath is withdrawn from the patient allowing the septal puncture to close, thus preventing communication of blood between the right and left atrium.

The expandable access sheath is configured to bend, or flex, around sharp corners and be advanced into the right atrium so that the longitudinal axis of its distal end is perpendicular to the atrial septal wall. Provision can optionally be made to actively orient or steer the sheath through the appropriate angles of between 20 to 120 degrees or more and to bend in one or even two planes of motion. The steering mechanism, in various embodiments, can be a curved guidewire and straight catheter, curved catheter and straight guidewire, a movable core guidewire, or a combination of the aforementioned. The expandable sheath also needs to be able to approach the right atrium from a variety of positions. In one embodiment, radial expansion of the distal end of the access sheath from a first smaller diameter cross-section to a second larger diameter cross-section is next performed, using a balloon dilator. The balloon dilator is subsequently removed from the sheath to permit passage of instruments that may not normally have been able to be inserted into the atrium of the heart. Once the sheath is in place, the guidewire may be removed or, preferably, it may be left in place. The atrial septum is gently dilated with radial force, preferably to a diameter of 10 mm or less, rather than being axially or translationally dilated by a tapered dilator or obturator. In most embodiments, the use of the expandable trans-septal sheath eliminates the need for multiple access system components.

In another embodiment of the invention, the expandable sheath comprises steerable members that eliminate the need for a 0.038-inch guidewire to be placed prior to sheath insertion and advancement. In another embodiment, the Brockenbrough-type needle, or septal penetrator, is integrated into the expandable sheath so that it can be used to puncture the atrium but does not need to be advanced and withdrawn through the sheath. The integral septal penetrator is actuated by the operator at the proximal end of the sheath. The controls at the proximal end of the sheath are operably connected to the septal penetrator at the distal end of the sheath by linkages, pressure lumens, electrical lines, or the like, embedded within the sheath and routed from the proximal end to the distal end. The septal penetrator is capable of bending with the articulating sheath distal region. In yet another embodiment, a reversible fixation device, or safety cushion, is provided at the distal end of the expandable sheath. The reversible fixation device is actuated by the operator at the proximal end of the sheath. The controls at the proximal end of the sheath are operably connected to the fixation device at the distal end of the sheath by linkages, pressure lumens, electrical lines, or the like, embedded within the sheath and routed from the proximal end to the distal end. The reversible fixation device can be an inflatable structure such as a balloon, a moly-bolt expandable structure, an expandable mesh, an umbrella, or the like, preferably positioned to expand within the left atrium. In an embodiment, the structure of the catheter or sheath is such that it is able to maintain a selectively rigid operating structure sufficient to provide stability against the atrial septum to support the advancement of trans-septal needles or penetrators. The sheath can be selectively stiffened, at least at its distal end, to provide a non-deflecting platform for support of instrumentation, such as the septal penetrator, which is passed therethrough.

In another embodiment of the invention, the proximal end of the expandable sheath comprises hemostasis or backflow check seals or valves to prevent blood loss and retrograde flow of air into the circulatory system. The hub of the sheath comprises such hemostasis seal. The seal comprises an annular soft elastomeric gasket that seals against catheters, instruments, and the dilator, inserted therethrough. The seal can further comprise a valve such as a stopcock, one-way valve such as a duckbill or flap valve, or the like to prevent significant blood loss and air entry when an instrument or catheter is removed from the lumen of the expandable sheath. The soft annular seal can further comprise a mechanism to compress the inner diameter of the seal radially inward, such as the mechanisms found on Tuohy-Borst valves. The hub further comprises one or more sideport for injection of contrast media such as Omnipaque, Renografin, or other Barium-loaded solutions, for example, or anticoagulant solutions such as heparin, coumadin, persantin, or the like, or for the measurement of pressure at or near the distal end of the sheath. The dilator hub comprises a central lumen with a Tuohy-Borst valve and one or more sideports for balloon inflation, said sideports operably connected to lumens in the dilator catheter for injection or withdrawal of fluids from a balloon at the distal end of the dilator and optionally for measurement of pressure at or near the dilator distal end. The dilator hub can also comprise a slide knob, a trigger, or other lever to actuate a septal puncture device at the distal end of the dilator. The dilator hub, the sheath hub, or both, can also comprise a handle, lever, or trigger mechanism to enable steering mechanisms at the distal end of the dilator, the sheath, or both, respectively.

The expandable sheath, in an embodiment, comprises radiopaque markers to denote the beginning and end of the expandable region, and the middle of the expandable region. The middle of the expandable region is useful in that it can be aligned with the atrial septum during the sheath expansion procedure. The sheath can comprise radiopaque materials such as gold wire, platinum wire, tantalum wire, or coatings of the aforementioned over a malleable, stainless steel, deformable reinforcing layer. Such complete radiopaque markings are especially useful for sheath dilation insofar as they allow the operator to more clearly visualize the extent to which the sheath has been dilated once the dilator is activated. In a preferred embodiment, a radiopaque marker band is affixed to the dilator substantially near the distal tip of the dilator so that the position of the distal tip can be observed and controlled relative to the wall of the left atrium or other cardiac structures. This radiopaque marker band can be a non-expandable, axially elongate tubular structure that is adhered to the non-expandable dilator shaft. Another non-expandable radiopaque marker band can be adhered to the dilator shaft at a position substantially corresponding to the proximal most dilating portion of the dilator or sheath. Another non-expandable radiopaque marker band can be adhered to the dilator shaft at a position substantially corresponding to the distal most dilating portion of the dilator or sheath. Thus, the atrial septum can be positioned with confidence between the two dilator radiopaque markers and dilation will be assured. The radiopaque marker bands can further be configured to appear different under fluoroscopy, for example by making the distal tip marker a single band, the distal dilation marker two bands, and the proximal dilator marker, three bands. Yet another configuration of radiopaque marker bands can be achieved by using malleable wire windings of gold, tantalum, platinum alloys, or the like, which are embedded within the folded and expandable sheath, preferably at or near the distal end of the sheath and, optionally, at or near the proximal end of the expandable portion of the sheath. These wire windings can expand with the sheath and can help show the extents of the sheath even after the dilator has been removed.

Since the hub of a Trans-Septal sheath requires many hemostasis valves and fluid input connectors or ports, the hub can be a longer structure than that on current guide catheters. Therefore, it may be required that a longer Brockenbrough needle is used to allow sufficient working length to provide for maneuverability within the cardiac anatomy. It can be beneficial to use Brockenbrough needles, which are longer than the standard 60-71 cm length, preferably those of 85 to 95 cm in length. Furthermore, the sheath hub length can be advantageously foreshortened by use of tightly grouped ports and minimum length Tuohy-Borst valves as well as "Y" connectors that are integrated into the hub, rather than being separately attached. Thus, the working length of the entire system is between 50 and 90 cm and preferably between 60 and 80 cm. In an exemplary embodiment, the working length of the entire system is 70 to 73 cm. The sheath hub length, including the length of the dilator hub, can range between 3 and 15 cm and preferably between 4 and 8 cm, the preferred length being appropriate if a shorter 70-cm or 71-cm long Brockenbrough needle is used.

In order to facilitate maneuvering the expandable trans-septal sheath into the right atrium and through the atrial septum, as well as for support of the sheath during catheter passage therethrough, it is beneficial to impart a curve into the trans-septal sheath, and optionally through the dilator. This curve is preferably a bend of between 20 to 120 degrees and preferably between 30 and 90 degrees. The bend can be in one plane or it can be in two orthogonal planes. An exemplary bend is to bend the sheath approximately 45 degrees out of plane 1 and approximately 50 degrees out of line in plane 2, which is orthogonal to plane 1. The radius of the curve can range between 2-cm and 12-cm and preferably between 3-cm and 10-cm in each of the two directions. Another example is a single plane curve of 90 degrees with a radius of around 3-cm to 12-cm. These bends are preferably imparted to the distal region of the non-expandable sheath tubing, just proximal to the expandable region. The bends can also be imparted through the expandable region but maintaining those bends in the expandable region may further require the use of a bent or curved shaped balloon, a resilient longitudinal support within the expandable region, a bent or curved dilator shaft, or both. The bending can be imparted to the tubing by placing the tubing over a curved mandrel and then heat-setting the tubing while over the mandrel. The tubing needs to be heated above glass-transition temperature, which is preferably above body temperature (37 degrees centigrade) for the heat set to be optimal. Materials used in the heat settable region can include, but not be limited to, polyethylene, PEN, PET, polyamide, polyimide, PEBAX, Hytrel, and the like. The expandable region of a trans-septal sheath need not be long and ranges between 0.5-cm and 20-cm with a preferred length of between 1-cm and 10-cm. By keeping the expandable region short, the region of the sheath comprising the bend, which allows the sheath have properties similar to those of a guiding catheter, is not in the expandable region, but rather just proximal to the expandable region. In other embodiments, methodologies of maintaining a bend within the expandable region are disclosed herein.

In yet another embodiment, the exterior of the sheath, and optionally the internal lumen of the sheath, can be coated with a lubricious coating comprising materials such as, but not limited to, silicone oil or a hydrophilic hydrogel comprising polyethylene glycol, polyether polyurethane, or the like. Other coatings can include antimicrobial coatings such as those fabricated from silver azide or anticoagulant coatings such as those comprising heparin.

In another embodiment, the proximal end of the sheath comprises a non-circular interior cross-section. The interior cross-section of the sheath can be oval, or it can comprise two or more completely walled off or partially walled off separate lumens. The sheath hub, which is affixed to the non-expandable proximal end of the sheath, can comprise two or more separate instrumentation ports, each of which are operably connected to a lumen or partial lumen within the sheath and which can advantageously comprise hemostasis valves. The instrumentation ports are especially useful for passage of, for example, multiple electrophysiology catheters, a mapping catheter and a therapeutic catheter, a ring catheter and an ablation catheter, or the like. Segregation of the multiple instruments can be useful to prevent binding or interference between the multiple catheters or instruments passed through the sheath. In yet another embodiment, the proximal end of the sheath has a non-circular cross-section that minimizes the overall cross-sectional area or circumference of a sheath configured to accept two or more catheters. This non-circular cross-section can be an oval, ellipse, rounded triangle, or the like. The non-circular cross section can, for example, reduce an 18 French OD catheter to around 15.5 French, using the same wall thickness and still retain the capability to accept two 8 French catheters within its internal lumen or lumens. Reduction in exterior cross-section is clearly useful in making the procedure as minimally invasive as possible and may make a procedure, which normally takes a cutdown, a percutaneous procedure.

In another embodiment, the guidewire port on the dilator hub is operably connected to a sideport. The sideport further comprises a flexible line and a luer connector and may further comprise an optional stopcock, needle valve, or a one way valve. The sideport can be a T-fitting, Y-fitting, or it can be integrally molded with the guidewire port on the dilator hub. The guidewire port can be preferably terminated at its proximal end with a hemostasis valve, a Tuohy-Borst fitting, or other valve or seal system.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 17A illustrates a side view of a collapsed, non-expanded trans-septal sheath, according to an embodiment of the invention;

FIG. 17B illustrates a side view of an expanded trans-septal sheath, according to an embodiment of the invention;

FIG. 17C illustrates a side view of an expanded trans-septal sheath with the dilator removed, according to an embodiment of the invention;

FIG. 20A illustrates a side view of the distal end of a trans-septal sheath and dilator comprising curvature near its distal end to facilitate trans-septal puncture, according to an embodiment of the invention;

FIG. 20B illustrates a side view of the distal end of a trans-septal sheath and dilator in partial cross section showing the distal tapered fairing and its relationship to the folded expandable distal region of the sheath, according to an embodiment of the invention;

FIG. 21A illustrates a side view of a hemostasis adapter configured to serve as a plug for a large central lumen of a sheath hub, according to an embodiment of the invention;

FIG. 21B illustrates the hemostasis adapter of FIG. 21A inserted into the central Tuohy-Borst valve of a sheath hub, according to an embodiment of the invention;

FIG. 22A illustrates a distal end of an expanded trans-septal sheath with the dilator removed, showing the malleable reinforcement structure, according to an embodiment of the invention; and FIG. 22B illustrates a distal end of an expanded trans-septal sheath with the dilator removed, showing the malleable reinforcement structure and a parallel wound radiopaque coil, according to an embodiment of the invention.

DETAILED DESCRIPTION OF THE PREFERRED EMBODIMENTS

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

In the description below, reference will be made to a catheter or a sheath, which can be an axially elongate hollow tubular structure having a proximal end and a distal end. The axially elongate structure further can have a longitudinal axis and has an internal through lumen that extends from the proximal end to the distal end for the passage of instruments, fluids, tissue, or other materials. The axially elongate hollow tubular structure can be generally flexible and capable of bending, to a greater or lesser degree, through one or more arcs in one or more directions perpendicular to the main longitudinal axis. The tubular structure generally has a generally circular cross-section but in other embodiments can have oval, rectangular or other cross-sectional shape. As is commonly used in the art of medical devices, the proximal end of the device is that end that is closest to the user, typically a cardiologist, surgeon, or electrophysiologist. The distal end of the device is that end closest to the patient or that is first inserted into the patient. A direction being described as being proximal to a certain landmark will be closer to the user, along the longitudinal axis, and further from the patient than the specified landmark. The diameter of a catheter is often measured in "French Size" which can be defined as 3 times the diameter in millimeters (mm). For example, a 15 French catheter is 5 mm in diameter. The French size is designed to approximate the circumference of the catheter, in millimeters, and is often useful for catheters that have non-circular cross-sectional configurations. While the original measurement of "French" used 7 (3.14159 . . . ) as the conversion factor between diameters in millimeters (mm) and French, the system has evolved today to where the conversion factor is 3.0.

Figure 1:
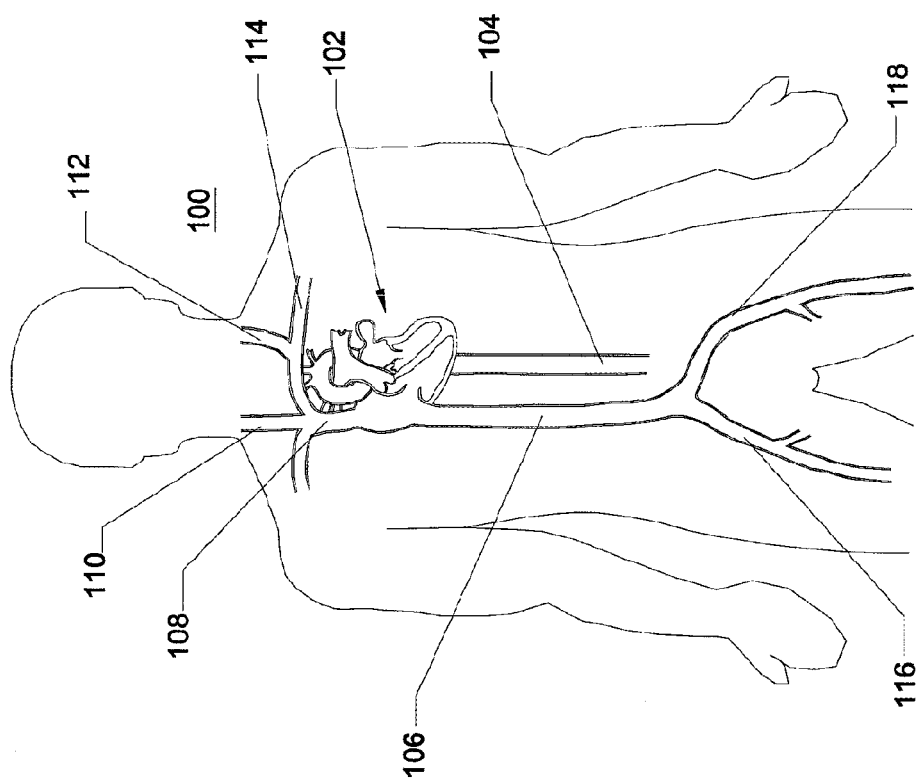
FIG. 1 is a front view schematic representation of the human venous circulatory system including the heart and the great veins.

FIG. 1 is a schematic frontal (anterior) illustration (looking posteriorly) of a human patient 100 comprising a heart 102, a descending aorta 104, an inferior vena cava 106, a superior vena cava 108, a right jugular vein 110, a left jugular vein 112, a subclavian vein 114, a right femoral vein 116 and a left femoral vein 118. In this illustration, the left anatomical side of the body of the patient 100 is toward the right of the illustration. FIG. 1 primarily illustrates components of the venous circulation.

Referring to FIG. 1, the heart 102 is a pump, the outlet of which is the aorta, including the descending aorta 104, which is a primary artery in the systemic circulation. The circulatory system, which is connected to the heart 102 further comprises the return, or venous, circulation. The venous circulation comprises the superior vena cava 108 and the inferior vena cava 106, which return blood from the upper extremities and lower extremities, respectively. The right and left jugular veins, 110 and 112, respectively, and the subclavian vein 114 are smaller venous vessels with venous blood returning to the superior vena cava 108. The right and left femoral veins, 116 and 118 respectively, return blood from the legs to the inferior vena cava 106. The veins carry blood from the tissues of the body back to the right heart, which then pumps the blood through the lungs and back into the left heart. Pressures within the venous circulation generally average 20 mm Hg or less. The arteries of the circulatory system carry oxygenated blood (not shown) from left ventricle of the heart 102 to the tissues of the body. The pressures within the arteries for a normal person undulate, with a modified triangle waveform, between a diastolic pressure of around 80 mm Hg to a systolic pressure of around 120 mm Hg. A hypotensive person may have arterial pressure lower than 120/80 mm Hg and a hypertensive person may have arterial pressures higher than 120/80 mm Hg. Systolic arterial pressures of 300 mm Hg can occur in extremely hypertensive persons.

Figure 2:
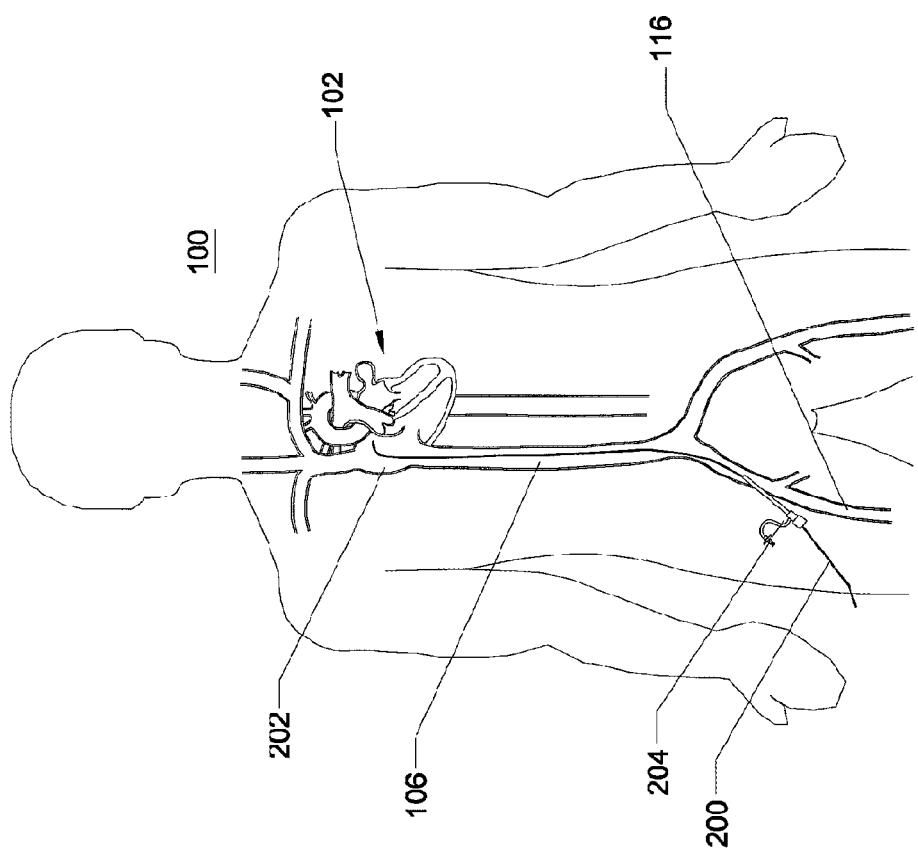
FIG. 2 is a front view schematic representation of the human venous circulatory system with a guidewire routed from the femoral vein into the right atrium.

FIG. 2 is a schematic frontal illustration, looking posteriorly from the anterior side, of the patient 100. A vascular introduction sheath 204 has been inserted into the right femoral vein 116 via a percutaneous puncture or incision. A guidewire 200 has been inserted through the introduction sheath 204 and routed, cranially, up the inferior vena cava 106 to the right atrium 202, one of the chambers of the heart 102. In this illustration, the left anatomical side of the patient 100 is toward the right. The guidewire 200 has been placed so that it can be used to track therapeutic or diagnostic catheters into a region of the heart 102.

Referring to FIG. 2, The venous circulation, through which the guidewire 200 has been routed, is generally at lower pressure between 0 and 20 mm Hg than is the systemic circulation, of which the descending aorta is a part. The pressure within the systemic circulation may range from 60 to over 300 mm Hg depending on the level of hypertension or hypotension existent in the patient. By accessing the heart through the venous circulation, the chance of hemorrhage from the catheter insertion site is minimized, as is the demand on the hemostasis valves built into any catheters used on the patient.

Figure 3:
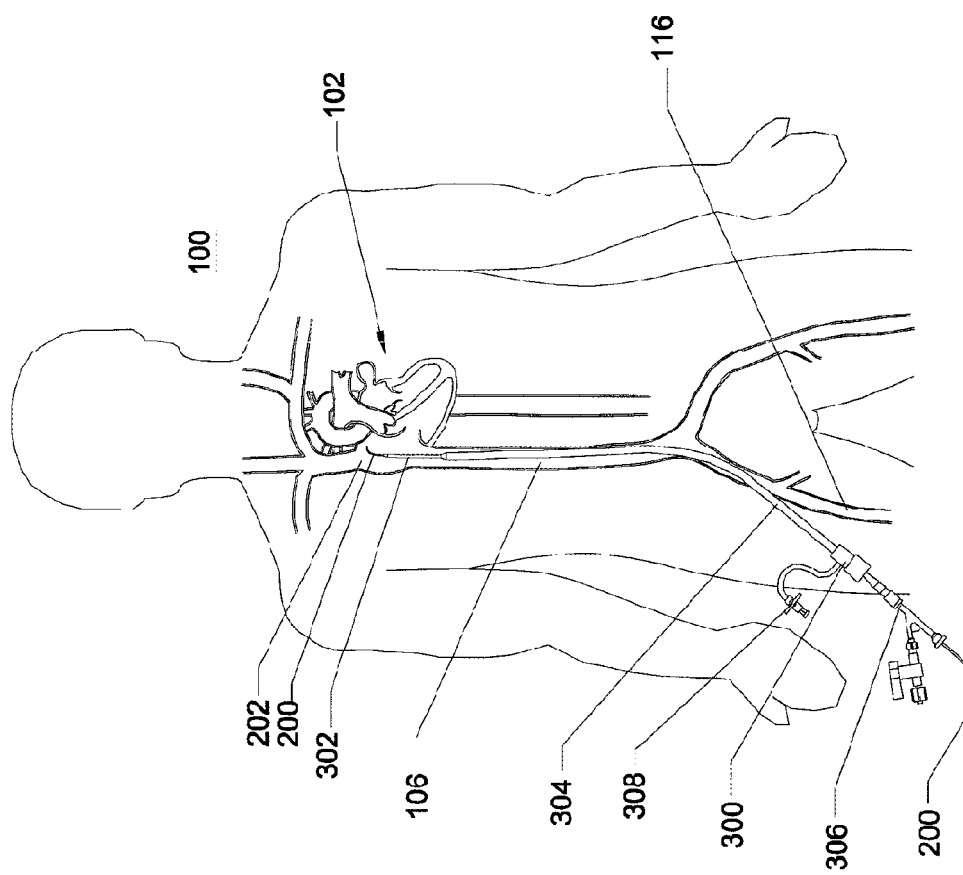
FIG. 3 is a front view schematic representation of the human venous circulatory system with an expandable sheath advanced into the right atrium, according to an embodiment of the invention.

FIG. 3 is a frontal illustration, looking posteriorly from the anterior side, of the patient 100. The vascular introduction sheath 204 of FIG. 2 has been removed from the right femoral vein 116 and a larger Trans-Septal Expandable Sheath 300 has been inserted into the venous circulation over the guidewire 200 and routed through the inferior vena cava 106 into the right atrium 202 of the heart 102. The expandable trans-septal sheath 300 further comprises a dilator 306, the proximal most part of which is shown in FIG. 3. The expandable trans-septal sheath 300 further comprises a proximal non-expandable region 304 and a distal expandable region 302.

Referring to FIG. 3, the venous circulation is filled with blood (not shown) that is somewhat depleted of oxygen and enriched with carbon dioxide as a result of interaction with body tissues. In the illustrated embodiment, the expandable region 302 of the expandable trans-septal sheath 300 is smaller in diameter than the proximal non-expandable region 304.

Figure 4:
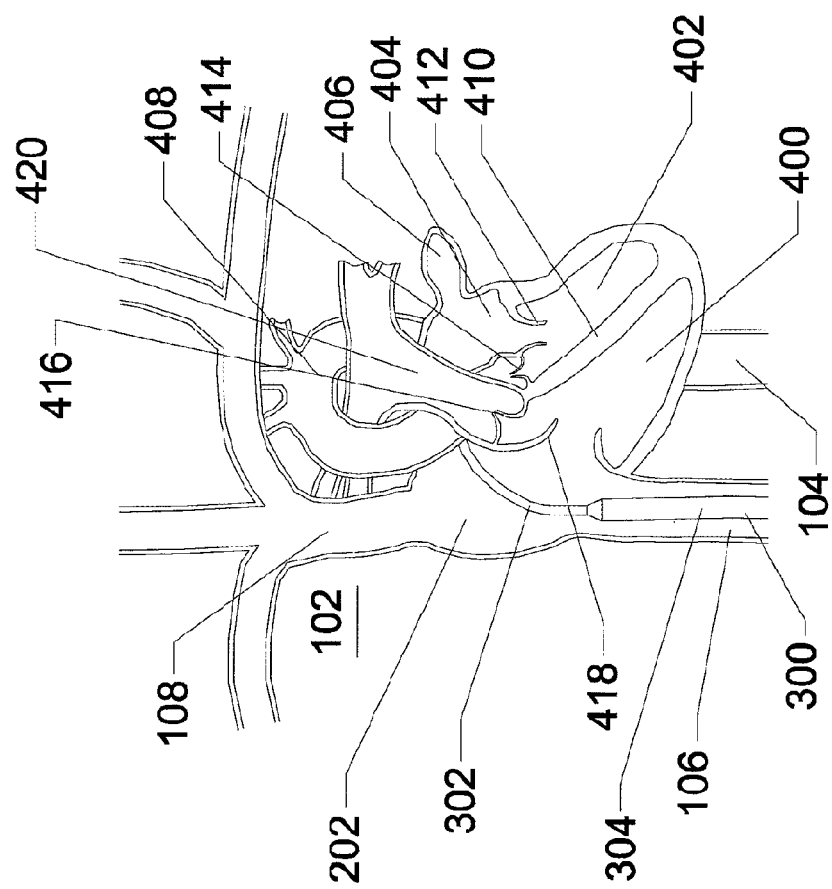
FIG. 4 is a cross-sectional illustration of the heart with the expandable sheath articulated and positioned within the right atrium and the guidewire removed, according to an embodiment of the invention.

FIG. 4 is a cross-sectional illustration of the heart 102, further comprising the descending aorta 104, the inferior vena cava 106, the superior vena cava 108, the right atrium 202, a right ventricle 400, a left ventricle 402, a left atrium 404, and a left atrial appendage 406. The heart 102 also comprises an aortic arch 408, a ventricular septum 410, a mitral valve 412, an aortic valve 414, a pulmonary valve 416, a tricuspid valve 418, and a pulmonary artery 420. The expandable region 302 of the sheath 300 is visible in the right atrium 202 and the proximal non-expandable region 304 of the expandable trans-septal sheath 300 is visible in the inferior vena cava 106.

Referring to FIG. 4, the expandable distal region 302 has been articulated or deflected in an arc so that its distal end rests against the atrial septum (not shown), the wall of myocardium that divides the right atrium from the left atrium. In this illustration, the atrial septum is obscured by the ascending aorta 602 (FIG. 6), that region of aorta between the aortic arch 408 and the aortic valve 414, as well as the pulmonary artery 420 and the pulmonary valve 416. The distal end of the distal sheath region 302 is positioned so that it rests within the Foramenal valley of the atrial septum, a naturally thin area of the atrial septum and a preferred landmark for continuing the procedure. The distal region 302 can be articulated, in an embodiment, with the use of an integral or removable internal steering mechanism. The distal region 302, in another embodiment, can be articulated using a movable core guidewire or a bent guidewire (not shown) inserted through the central lumen of the distal region 302 of the sheath 300.

Figure 5:
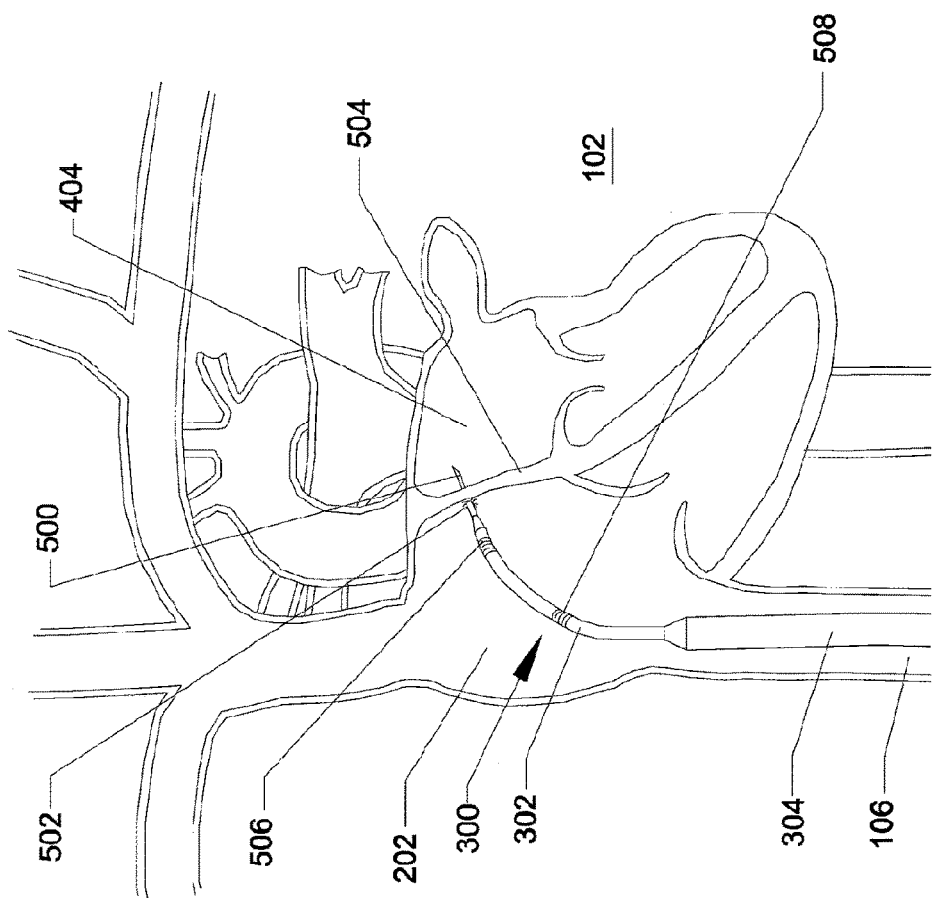
FIG. 5 is a cross-sectional illustration of the heart with the expandable sheath positioned at the atrial septum and the septal penetrator advanced across the atrial septum into the left atrium, according to an embodiment of the invention.

FIG. 5 is a cross-sectional illustration of the heart 102, showing the atrial septum 504. The ascending aorta 602 (FIG. 6), aortic valve 414, pulmonary artery 420, and pulmonary valve 416 of FIG. 4 have been removed from this illustration for clarity and to show the atrial septum 504. The distal expandable region 302 of the sheath 300, substantially located within the right atrium 202, is shown with its long axis perpendicular to the atrial septum 504. The proximal end 304 of the sheath 300 is shown resident within the inferior vena cava 106. A septal penetrator 500 is shown extended through a puncture 502 in the atrial septum 504 and is routed into the left atrium 404. The distal expandable region 302 further comprises the foldable distal radiopaque marker 506 and the proximal radiopaque marker 508.

Referring to FIG. 5, the septal penetrator 500 is a needle or axially elongate structure with a sharp, pointed distal end. The septal penetrator 500 can be resident within the guidewire lumen of the dilator 306 (FIG. 3), which can be removably resident within the distal expandable region 302. The septal penetrator 500 can be actuated at the proximal end of the sheath 300. The septal penetrator 500 can be operably connected to a control mechanism such as a button, lever, handle, trigger, etc., which can be affixed, permanently or removably, at the proximal end of the dilator 306 by way of a linkage, pusher rod, electrical bus, or the like that runs the length of the dilator 306. The penetrator 500 can also be integrated into the sheath 300 but the removable dilator 306 can be more advantageous. Care must be taken not to have the septal penetrator 500 pierce the wall of the left atrium 404 opposite the atrial septum 504 so length control and advance control are important as can be guidance, either by fluoroscopy, MRI, ultrasound, or the like. Further care must be taken not to inadvertently pierce the aorta in the region upstream or anatomically proximal to the aortic arch 408 (FIG. 4). The distal expandable region 302 can be bent, deflected, or articulated through an angle of between 30 and 120 degrees to achieve approximate perpendicularity with the atrial septum 504. The septal penetrator 500 can be solid, it may be hollow like a hypodermic needle, or it may have a "U" or "C"-shaped cross-section. The center or core of a hollow, "C", or "U"-shaped septal penetrator can be filled with a guidewire or other core element to prevent incorrect tissue penetration. The septal penetrator 500 can be rigid or it can be flexible but retain column strength. Such flexible configurations can comprise cutouts in the wall of the penetrator 500 or guidewire-like construction. The septal penetrator 500 can be initially straight or it can be initially curved. The septal penetrator 500 can be fabricated from shape memory material such as nitinol and heat treated to cause curving once the material is heated from martensitic to austenitic temperatures. Such heating can be performed using electrical heating, hot water injection, or the like. Preferred temperatures for the austenite finish temperature, in this application range from 25 degrees to around 42 degrees centigrade. Higher temperatures require more heating and rely on hysteresis to minimize the return to the martensite phase when the heating temperature is removed. The distal foldable radiopaque marker 506 and the proximal foldable radiopaque marker 508 can be fabricated as either flat or round wire from metals such as, but not limited to, gold, platinum, iridium, titanium, tantalum, and the like. The distal foldable radiopaque marker 506 can be advantageously located near the distal end of the foldable section 302 while the proximal foldable radiopaque marker 508 can be advantageously located 1 to 10 cm, and preferably 2 to 4 cm proximal to the distal foldable marker 506. The foldable radiopaque markers 506 and 508 are malleable and embedded within the wall of the foldable section 302 and can be deformed and folded with a linear crease to minimize their diameters to facilitate delivery of the sheath 300.

Figure 6:
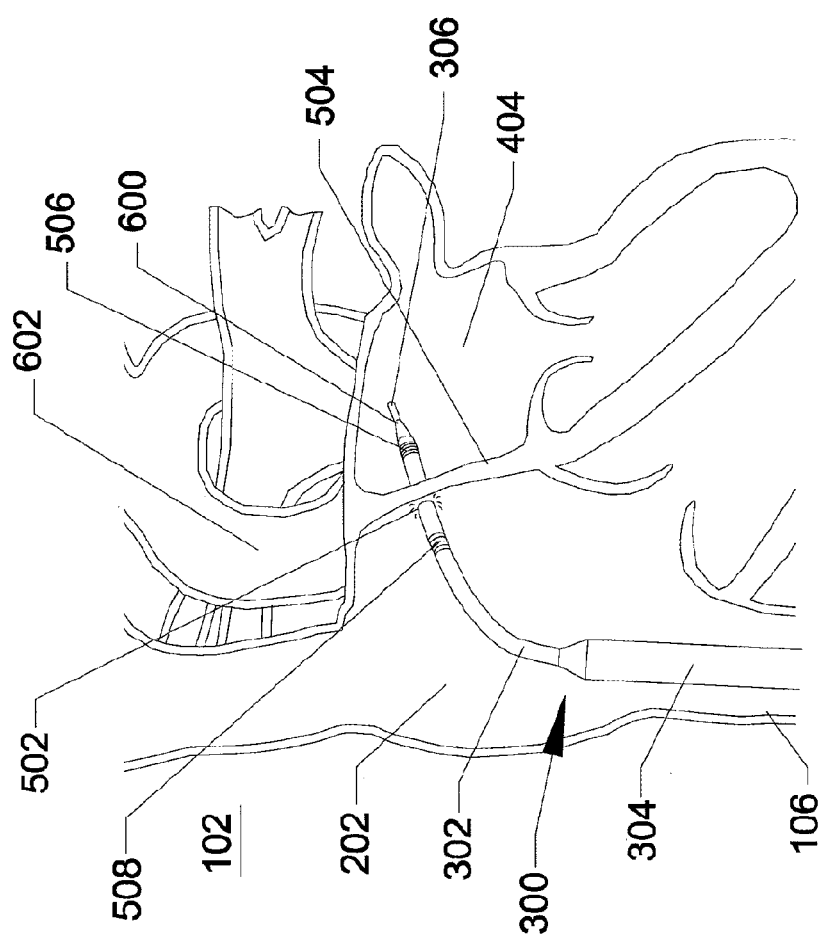
FIG. 6 is a cross-sectional illustration of the heart with the expandable sheath advanced into the left atrium across the atrial septum and the septal penetrator withdrawn into the dilator of the expandable sheath, according to an embodiment of the invention.

FIG. 6 illustrates a cross-sectional view of the heart 102 showing the distal expandable region 302 having been advanced across the atrial septum 504 from the right atrium 202 and into the left atrium 404. The tapered tip 600 of the dilator 306 leads the distal end of the expandable region 302 through the septal puncture 502 created by the penetrator 500. That region of the ascending aorta 602 that does not obscure this anterior view of the atrial septum 504 is shown. The proximal non-expandable region 304 has advanced, to follow the advancing distal expandable region 302, so that the proximal region 304 can be located not only in the inferior vena cava 106 but also within the right atrium 202. The distal expandable region 302 further comprises the proximal foldable radiopaque marker 508 and the distal foldable radiopaque marker 506. The markers 506 and 508 are shown in their radially collapsed, folded configuration.

Referring to FIG. 6, the expandable access sheath 300 can be pre-assembled with its internal dilator 306. The dilator 306 can be, in an embodiment, a catheter with a dilatation balloon (not shown) affixed to a dilator shaft. The dilatation balloon can be preferably an angioplasty-type, non-elastomeric balloon and can be fabricated from materials such as, but not limited to, PET, polyamide, cross-linked polyolefins, or the like. The dilator shaft can be terminated at its proximal end with an inflation port that can be operably connected to a lumen within the dilator shaft. The lumen within the dilator shaft can be operably connected to the interior of the balloon by way of scythes or other openings. The tapered tip 600 can be affixed to the distal end of the dilator 306 and can be fabricated from Hytrel, a thermoplastic elastomer such as C-Flex, or from elastic polymers such as silicone elastomer, polyurethane, or the like. The tapered tip 600 can have a general funnel shape tapering from small at the distal end to large at the proximal end. In another embodiment, the tapered dilator tip 600 can have a complex taper with two or more angles and can also include intermediate cylindrical, non-tapered, regions. The tapered tip 600 can be made to expand with the distal end of the balloon and then shrink down with the balloon when it is deflated, facilitating withdraw through the lumen of the expanded distal region 302 of the sheath 300. The tapered tip 600 can be asymmetric to substantially match the cross-sectional configuration of an expandable sheath section that can be folded and has inherently axial asymmetry. The foldable radiopaque markers 506 and 508 are visible under fluoroscopy or X-ray visualization and can be used to guide the sheath 300 across the atrial septum 504. The distal foldable radiopaque marker 506 can be configured to be located within the left atrium and across the atrial septum 504 when it is correctly located in its target position prior to expansion. The proximal foldable radiopaque marker 508 can be configured to be located within the right atrium and proximal to the atrial septum 504 such that the markers approximately evenly straddle the atrial septum 504. The atrial septum 504 can be visualized as a dark spot on fluoroscopy if it is painted with radiopaque contrast media injected through the central lumen of the Brockenbrough needle (not shown).

Figure 7:
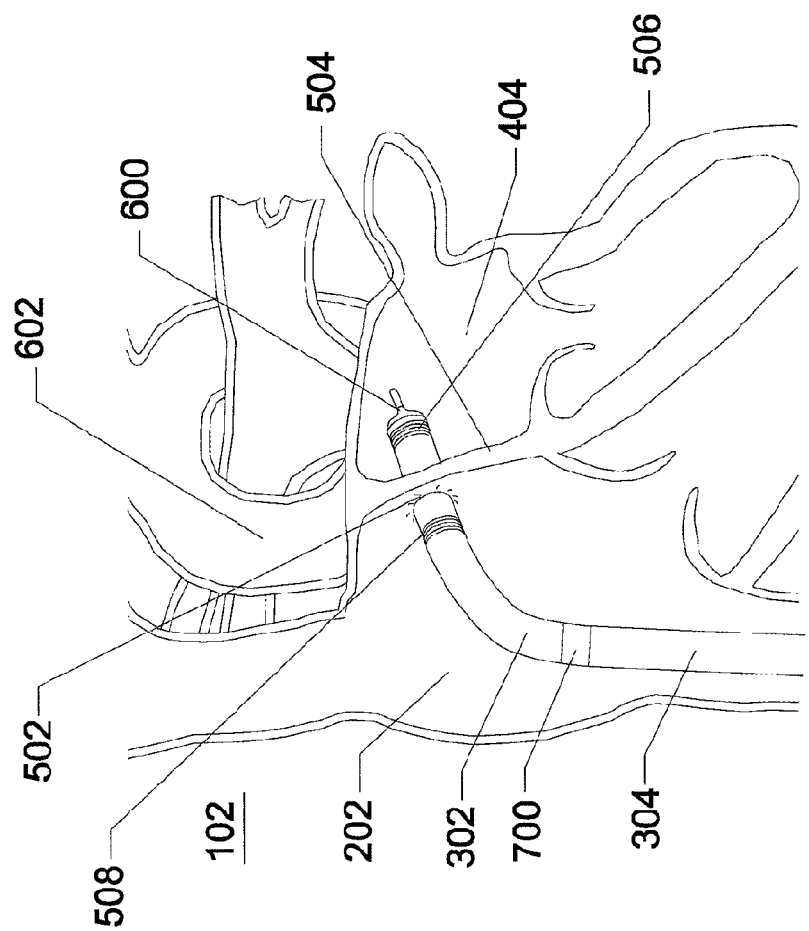
FIG. 7 is a cross-sectional illustration of the heart with the expandable sheath dilated at its distal end by the dilator, according to an embodiment of the invention.

FIG. 7 illustrates a cross-sectional view of the heart 102 showing the distal expandable region 302 having been radially expanded while placed across the atrial septum 504 between the right atrium 202 and the left atrium 404. The distal expandable region 302 is now generally of the same diameter as the proximal region 304. The distal expandable region 302 further comprises the proximal foldable radiopaque marker 508 and the distal foldable radiopaque marker 506. The markers 506 and 508 are shown in their radially expanded, full diameter configuration. The distal foldable radiopaque marker 506 and the proximal foldable radiopaque marker 508 are shown correctly positioned and substantially equidistant on opposite sides of the atrial septum 504. The transition zone 700 can be that region connecting the distal region 302 and the proximal region 304. The dilator balloon resides within the transition zone 700 as well as the distal expandable region 302. The puncture 502 in the atrial septum 504 has now been dilated using radial dilation means and the distal end of the sheath 302 can be resident within the left atrium 404. The dilator tip 600 remains within the left atrium 404. The use of radial dilation can be considered beneficial and superior to translation dilation by tapered axially translating dilators with regard to tissue healing and wound closure. The radial dilation allows the septal transit to be performed with relatively small expandable tips in the range of 7 to 10 French. Following transit of the septum through the perforation created by the penetrator, a small sheath with a smooth, tapered, distal transition can be advanced readily through the penetration. The expandable region 302 can then be dilated radially, opening up the septal penetration to any size from 12 to 30 French. Such radially, or circumferentially, dilated openings are known to heal more completely, following removal of the instrument. In another embodiment, the expandable region 302 can be expanded by forcing an inner dilator (not shown) distally along the long axis of the sheath 300 to force the expandable region 302 to dilate diametrically. Such axial translation dilation can be generated by way of a pusher affixed to the inner dilator at its distal end and a handle or mechanical lever at the proximal end of the sheath 300. The expandable region 302 can be elastomeric or comprise one or more longitudinal folds, which cause the circumference, and thereby the diameter, to be small until dilated.

Figure 8:
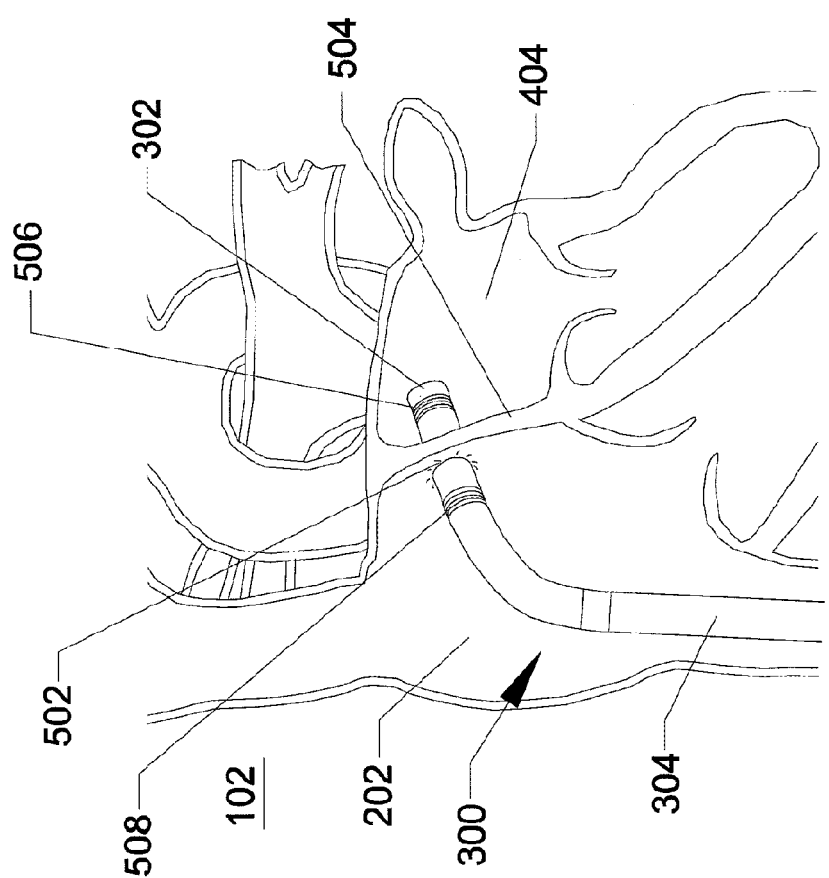
FIG. 8 is a cross-sectional illustration of the heart with the expandable dilator withdrawn from the sheath leaving a large central lumen for instrument passage into the left atrium, according to an embodiment of the invention.

FIG. 8 illustrates a cross-sectional view of the heart 102 wherein the distal end of the distal expandable region 302 can be resident within the left atrium 404 and can be located across the atrial septum 504. The tip 600 (FIGS. 6 and 7) of the dilator 306 (not shown) has been removed and withdrawn from the proximal end of the sheath 300. In this configuration, the sheath 300 retains a large, central lumen capable of passing instrumentation, catheters, or the like into the left atrium 404. The size of the sheath 300 can be substantially the same whether in the distal expandable region 302 or the proximal non-expandable region 304. The central lumen of the sheath can be exposed to pressure within the left atrium 404, said left atrial pressures being 20 mm Hg or less. This large sheath 300 can be capable of delivering one, two, or more catheters into the left atrium 404 without the need for more than one atrial septal puncture 502. The distal expandable region 302 further comprises the proximal foldable radiopaque marker 508 and the distal foldable radiopaque marker 506. The markers 506 and 508 are shown in their radially expanded, unfolded configuration and the sheath 300 is correctly positioned across the atrial septum 504 to provide catheter access to the left atrium through the sheath 300. In another embodiment, only a distal foldable marker 506 can be comprised by the sheath 300, while in yet another embodiment, only a proximal foldable radiopaque marker 508 can be comprised by the sheath.

Figure 9:
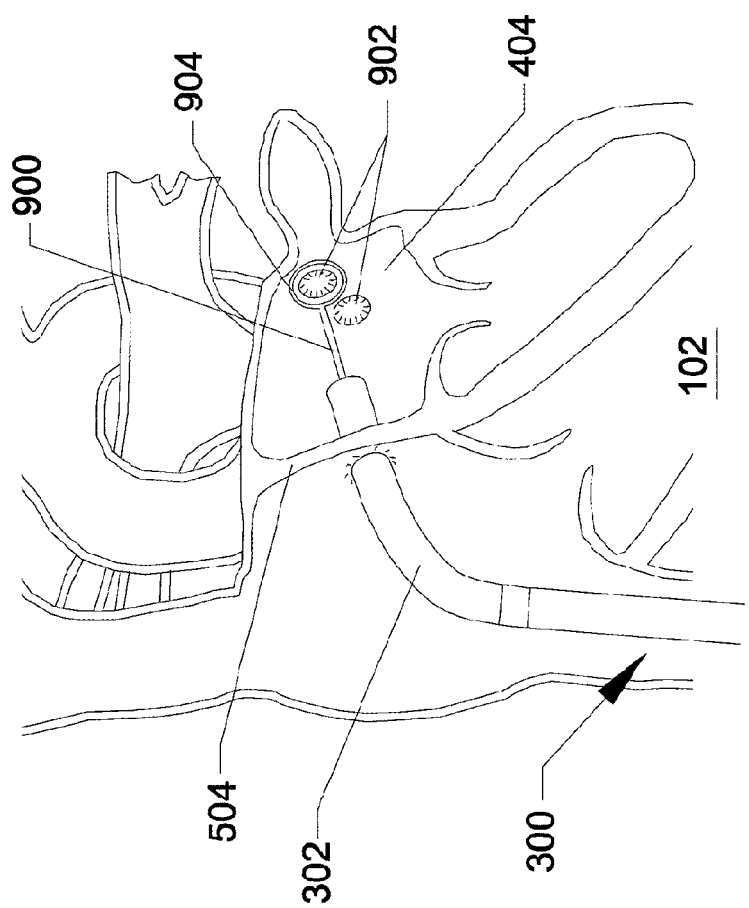
FIG. 9 is a cross-sectional illustration of the heart with an electrophysiology therapeutic catheter advanced through the central lumen of the expanded sheath into the left atrium, according to an embodiment of the invention.

FIG. 9 illustrates a cross-sectional view of the heart 102 wherein the distal end of the distal expandable region 302 can be resident within the left atrium 404 and can be located across the atrial septum 504. Two of the outlets for the pulmonary veins 902 are shown within the left atrium 404. The tissue around the pulmonary veins 902 is often a site for re-entrant waveforms that cause atrial arrhythmias. Ablation of this tissue using heat or extreme cold temperatures (cryogenics) can alleviate the arrhythmias. In the illustrated embodiment, an electrode 904 that emits Radiofrequency (RF) energy has been introduced at the end of an electrophysiology catheter 900 into the right atrium 404 through the expandable sheath 300. The electrode 904 shown can be a round electrode called a lasso electrode and can be capable of heating and ablating a ring of tissue in a single operation. Single point electrodes 904 can create line or ring ablations but must be drawn slowly along the tissue to ablate the desired pattern. Such electrode movement can be difficult to achieve at the end of a curved 100-cm long, or longer, catheter being monitored by fluoroscopy or ultrasound. The heating electrodes can deliver energies such as microwaves, radio frequencies, high-intensity focused ultrasound (HIFU), and the like. Because these ring electrodes 904 are large in diameter, they may be advantageously placed through very large sheaths such as the expandable trans-septal sheath 300.

Figure 10:
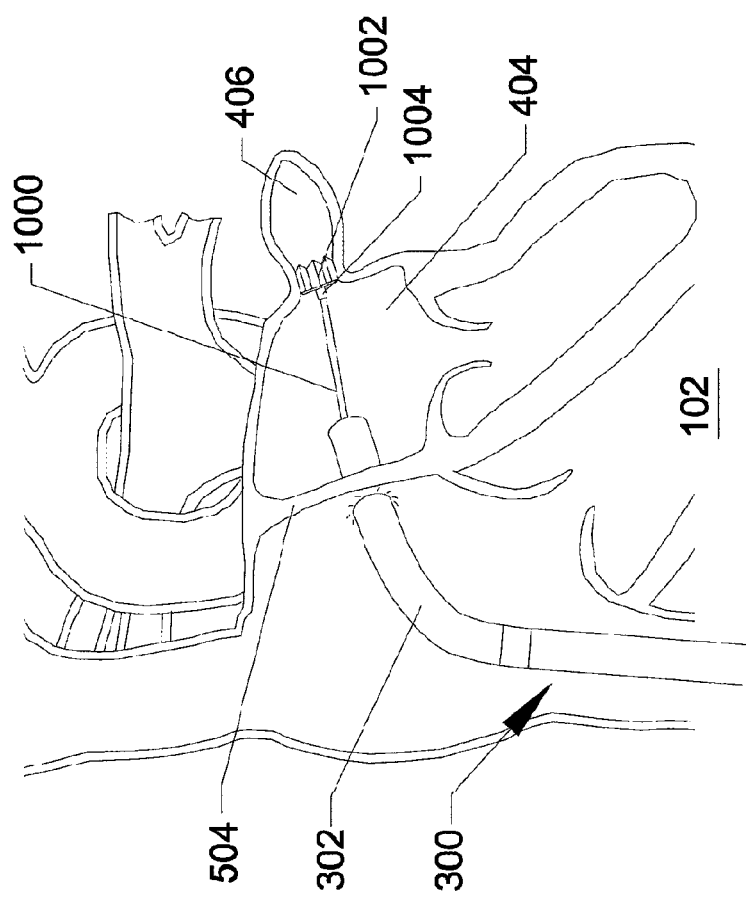
FIG. 10 is a cross-sectional illustration of the heart with an atrial septal plug delivery catheter advanced through the central lumen of the expanded sheath into the left atrium, according to an embodiment of the invention.

FIG. 10 illustrates a cross-sectional view of the heart 102 wherein the distal end of the distal expandable region 302 of the expandable trans-septal sheath 300 can be resident within the left atrium 404 and can be located across the atrial septum 504. A delivery catheter 1000 for an implantable device 1002 can be routed through the expandable sheath 300. In this embodiment, the implantable device 1002 can be an expandable plug capable of closing off the opening between the left atrium 404 and the left atrial appendage 406. The implantable device 1002 can be releasably affixed to the distal end of the catheter 1000 by a releasable coupler 1004, activated by a linkage extending between the distal coupler 1004 and the proximal end of the delivery catheter 1000. Such left atrial appendage 406 plugs or filters have been shown to reduce emboli generation by the left atrial appendage 406 in conditions where the left atrium 404 is in a state of atrial fibrillation, or uncoordinated muscle contraction. Atrial fibrillation, while not life threatening, results in reduced cardiac output and exercise tolerance. It can be also associated with a high rate of cerebrovascular embolic stroke. Left atrial appendage implants 1002 are radially collapsible during delivery. They are generally delivered through 14 French or larger catheters and a radially expandable delivery sheath would be advantageous.

Figure 11:
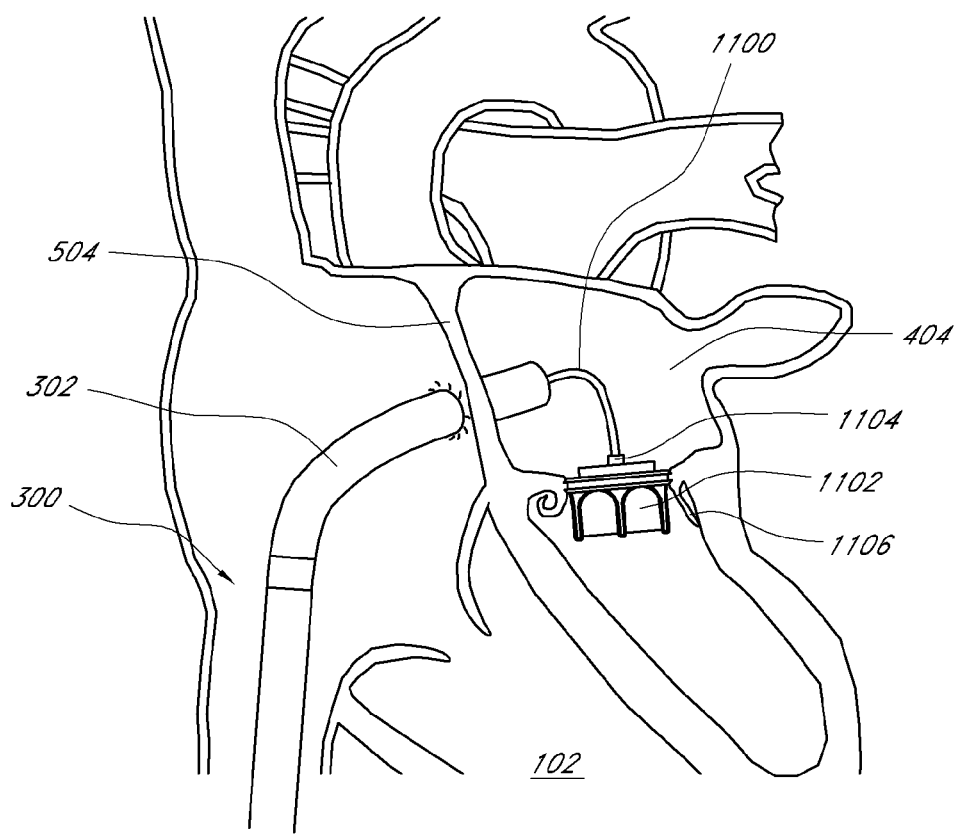
FIG. 11 is a cross-sectional illustration of the heart with a collapsible mitral valve prosthesis delivery catheter advanced through the central lumen of the expanded sheath into the left atrium, according to an embodiment of the invention.

FIG. 11 illustrates a cross-sectional view of the heart 102 wherein the distal end of the distal expandable region 302 of the expandable trans-septal sheath 300 can be resident within the left atrium 404 and can be located across the atrial septum 504. A mitral, or aortic, valve implant delivery catheter 1100 can be routed through the expandable sheath 300. The catheter 1100 can be controllably, releasably, affixed to the inlet side of a collapsible, mitral valve prosthesis 1102 by a coupler 1104. The coupler 1104 can be operably connected to the proximal end of the delivery catheter 1100 by a linkage. The delivery catheter 1100 can be required to articulate to reach the mitral valve orifice to place the mitral valve prosthesis 1102. The mitral valve prosthesis 1102 can be expanded so that it engages the remnants of the diseased mitral valve leaflets 1106 so that it can be secured in place. Such a prosthesis can be necessarily large, (up to 35 mm diameter fully expanded) and requires a very large trans-septal catheter (20 to 30 French), even for a radially collapsed device. The expandable trans-septal catheter 300 would allow placement of such large devices with minimal damage to the atrial septum 504. Similar techniques can be used for placement of an aortic valve with access gained through a femoral, subclavian, or iliac artery.

Figure 12:
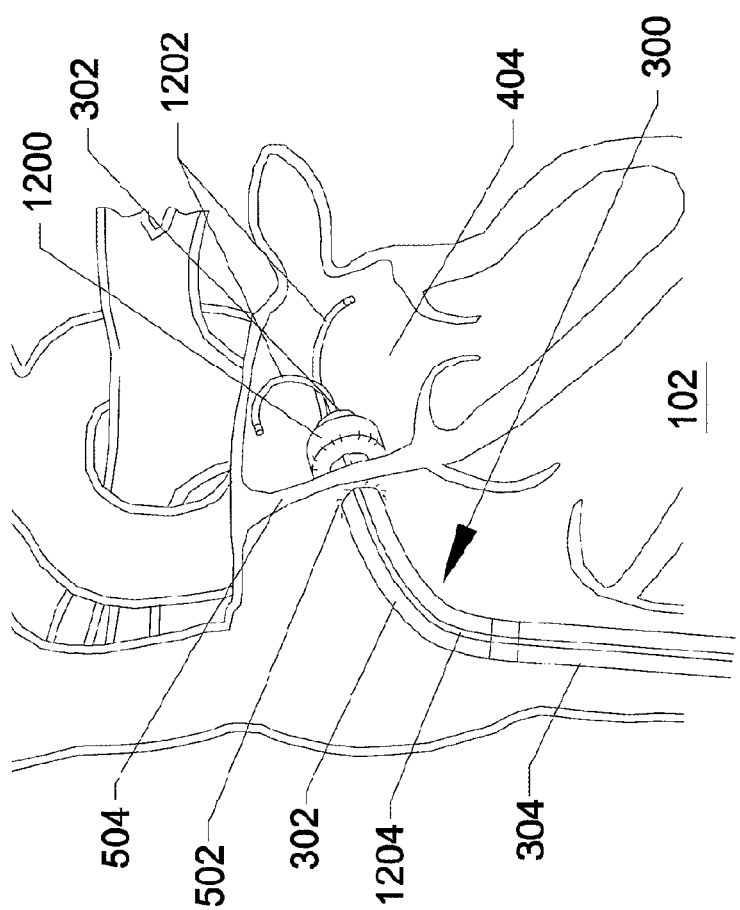
FIG. 12 is a cross-sectional illustration of the heart with the expandable sheath traversing into the left atrium and secured in place with a left atrial anchor system, according to an embodiment of the invention.

FIG. 12 illustrates a cross-sectional view of the heart 102 wherein the distal end of the distal expandable region 302 of the expandable trans-septal sheath 300 can be resident within the left atrium 404 and can be located across the atrial septum 504. A distal anchor 1200 is shown inflated within the left atrium 404 for the purpose of stabilizing the sheath 300 so that its expandable region 302 cannot be inadvertently pulled out of the left atrium 404. Two electrophysiology catheters 1202 are shown extending into the left atrium 404 out the distal end of the expandable region 302. An inflation lumen 1204 is illustrated riding on the surface of the sheath 300 in both the proximal region 304 and the distal expandable region 302. The inflation lumen 1204 can be operably connected to an inflation port and valve at the proximal end of the sheath 300 and can be operably connected to the interior of the distal anchor 1200. The distal anchor, in this embodiment, can be a balloon. The balloon can be either non-compliant like an angioplasty balloon or compliant like a Foley balloon, the latter of which can be fabricated from silicone elastomer, latex rubber, polyurethane, or the like. Non-compliant balloons can be made from cross-linked polyethylene or polypropylene or from stretch blow molded polyethylene terephthalate, polyamides, or the like. In another embodiment, a second balloon 1506 (FIG. 15) can be placed so that it expands within the right atrium 202 against the atrial septum 504. Inflation of the second balloon 1506 can be performed through the same inflation lumen 1204 as that used for the distal anchor 1200. Such inflation through the same inflation lumen 1204 would be substantially simultaneous with the distal anchor 1200. Inflation of any of the balloons can be performed using a high-pressure inflation device that is operably connected to an inflation lumen 1204. The high-pressure inflation device can be used to inject fluid such as, but not limited to, saline, contrast media, carbon dioxide, or the like into the balloon to generate the desired inflation and diameter increase. The second balloon 1506 would prevent distal migration of the sheath 300. In another embodiment, a dumbbell shaped balloon would replace the two separate balloons. The small diameter part of the dumbbell balloon can be configured to reside within the puncture site 502. Such dumbbell balloon can be preferably fabricated as a non-compliant balloon. The distal anchor could also be fabricated as a moly-bolt, umbrella, expandable braid, or other expandable structure activated by a linkage to the proximal end of the sheath. Fabrication of the distal anchor can be achieved using materials such as, but not limited to, polyolefins such as polyethylene or polypropylene, polyamide, polyurethane, polyester, elastomeric materials, Hytrel, Pebax, or the like.

Figure 13:
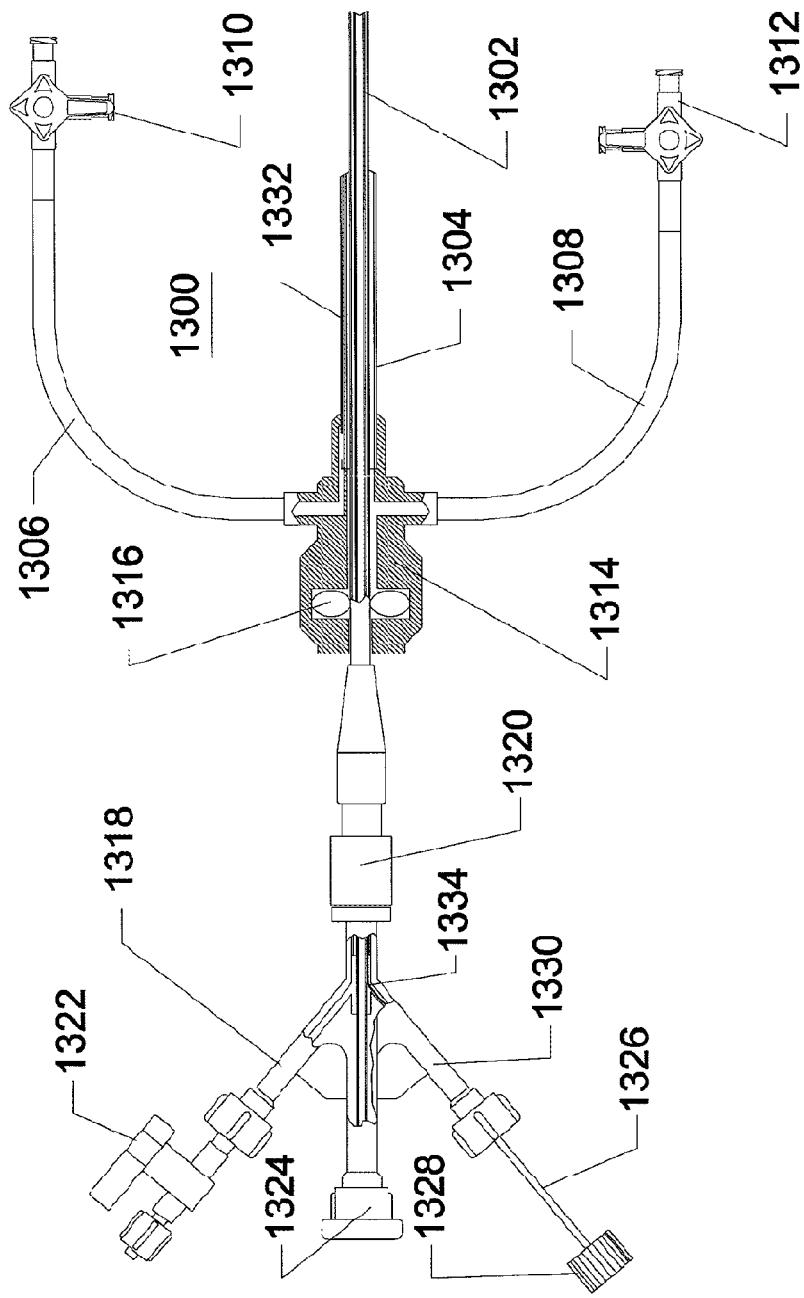
FIG. 13 is a cross-sectional illustration of the expandable sheath showing the proximal sheath and dilator hubs along with various hemostasis valves, actuators, and seals, according to an embodiment of the invention.

FIG. 13 illustrates a longitudinal cross-section of the proximal end 1300 of an expandable trans-septal sheath system. The proximal end 1300 comprises a dilator shaft 1302, a sheath shaft 1304, an anchor inflation line 1306, a fluid infusion line 1308, an anchor line stopcock 1310, a fluid infusion valve 1312, a sheath hub 1314, a sheath valve 1316, a dilator inflation port 1318, a dilator hub 1320, a dilation stopcock 1322, a guidewire port valve 1324, a penetrator shaft 1326, a penetrator knob 1328, a penetrator spring (not shown), a penetrator access port 1330, an anchor inflation lumen 1332, and a penetrator linkage 1334.

Figure 14:
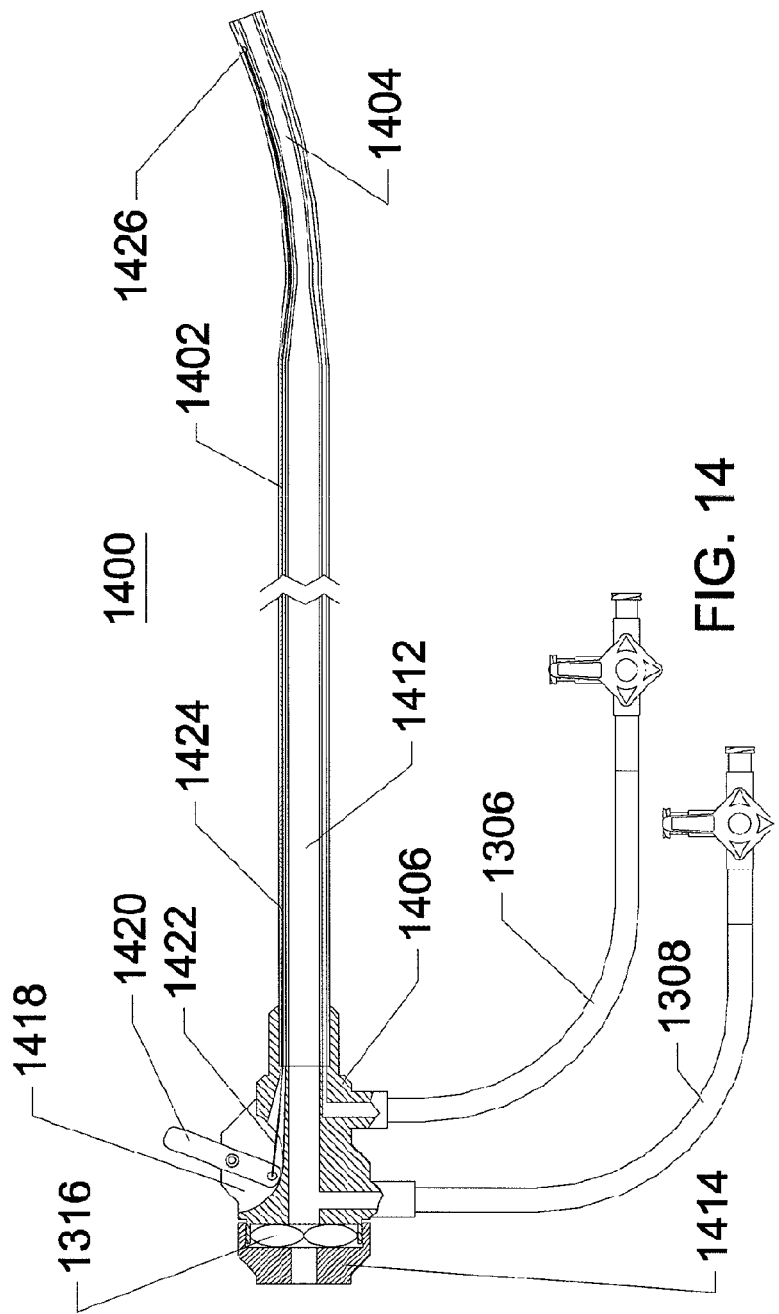
FIG. 14 is a cross-sectional illustration of the expandable sheath showing a deflection mechanism, according to an embodiment of the invention.

FIG. 14 illustrates a longitudinal cross-section of an articulating expandable trans-septal sheath 1400. The articulating, expandable sheath 1400 further comprises a proximal region 1402, a distal expandable region 1404, a sheath hub 1406, a transition zone 700, a central lumen 1412, a steering linkage lumen 1424, an anchor inflation line 1306, a fluid infusion line 1308, a compression cap 1414, a variable valve element 1316, a lever support 1418, a steering lever 1420, a steering linkage 1422, and a steering linkage distal fixation point 1426. In this embodiment, the articulation can be generated by tension or compression force in the steering linkage 1422 being applied to the fixation point 1426 affixing the steering linkage 1422 to the distal end of the distal expandable region 1404. The distal expandable region can be flexible and can be made preferentially more flexible in the region just proximal to the distal fixation point 1426. The lever 1418 provides mechanical advantage and can be used with ratchets, locks, friction elements, or the like to restrict movement of the lever 1418 and consequently the linkage 1422 when manual pressure is removed. The distal end of the sheath 1400 is shown bent, or articulated, into an arc and the lever 1420 can be correspondingly moved forward, relative to the hub 1406, to cause tension in the linkage 1422. A second lever support 1418, steering lever 1420, steering linkage 1422, distal fixation point 1426 and steering linkage lumen 1424 can be added, in another embodiment, to permit articulation of the distal region 1404 in a second direction.

Figure 15:
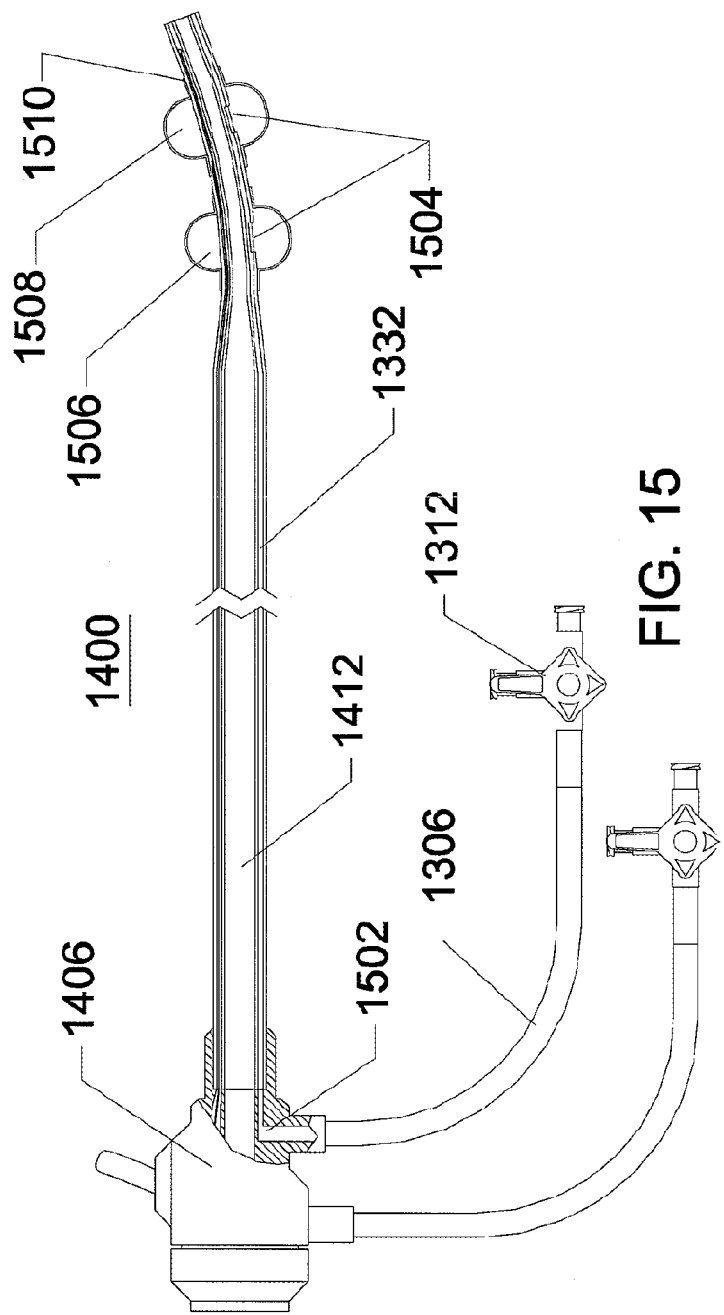
FIG. 15 is a cross-sectional illustration of the expandable sheath showing a distal anchor mechanism, according to an embodiment of the invention.

FIG. 15 illustrates a longitudinal cross-section of an articulating expandable sheath 1400 further comprising a distal anchor 1508, a proximal anchor 1506, and a plurality of anchor bonds 1510. The sheath 1400 further comprises an anchor inflation lumen 1332, a plurality of scythes 1504, an anchor inflation manifold 1502, an anchor inflation line 1306, an anchor inflation valve 1312, a hub 1406 and a central sheath lumen 1412. The distal anchor 1508 and the proximal anchor 1506 are shown as balloons that are inflated with fluid, preferably saline, water, or radiopaque contrast media. Inflation occurs through the anchor inflation valve 1312, the anchor inflation line 1306, the anchor inflation manifold 1502 within the hub 1406, and the anchor inflation lumen 1332, which are all operably connected. Fluid pressure is added or removed to the balloons 1506 and 1508 through the scythes 1504, which are holes or ports in the wall of the sheath 1400 that expose the region inside the distal anchor 1508 and proximal anchor 1506 to the fluid pressure of the anchor inflation lumen 1332.

Figure 16:
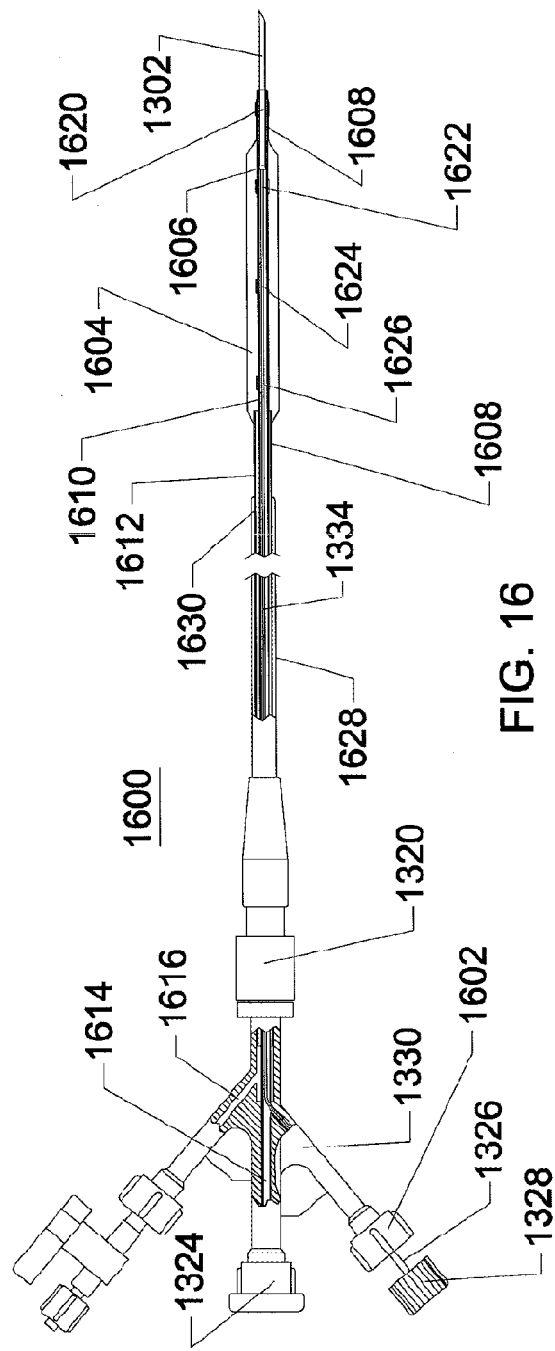
FIG. 16 is a cross-sectional illustration of the expandable sheath showing an atrial septal penetrator integral to the dilator, according to an embodiment of the invention.

FIG. 16 illustrates a longitudinal cross-section of a dilator 1600 suitable for use with an expandable trans-septal sheath 1400 (FIG. 15). The dilator 1600 further comprises a dilator hub 1320, a guidewire port with valve 1324, a penetrator access port 1330, an optional penetrator shaft 1326, an optional penetrator knob 1328, a penetrator spring (not shown), an optional penetrator linkage 1334, an optional penetrator 1302, an optional penetrator coupler 1606, an optional penetrator port closure 1602, an inner dilator tube 1610, an outer dilator tube 1612, a filler tube 1628, further comprising an optional filler tube distal bond 1630, a dilatation balloon 1604, a plurality of balloon bonds 1608, and a plurality of radiopaque markers 1620, 1622, 1624, 1626. The penetrator linkage 1334 and the penetrator 1302 can be solid, coiled, hollow tubes, or C-shaped. The C-shaped embodiment can be capable of further accepting a guidewire in the guidewire lumen 1614 at the same time as the penetrator 1302 and penetrator linkage 1334. The spring (not shown) can be located between the penetrator knob 1328 and the penetrator port closure 1602 and allows the penetrator 1302 to be advanced temporarily and then retracted to its safety position automatically. The guidewire can serve the function of plugging a central hole or hollow within the penetrator 1302. The penetrator 1302 can be a curved or a straight needle, or it may be fabricated from shape memory materials such as nitinol and be configured to be inserted straight but bend upon exposure to Ohmic heating, body temperature, hot water flushed therethrough, or the like. The dilator balloon 1604 can be preferably an angioplasty-type unfurling balloon with bonds at its proximal and distal end. The balloon 1604 can be fabricated from high-strength materials such as, but not limited to, PET, polyamide, cross-linked polymers, polyethylene, and the like. The balloon 1604 and dilator 1600 can be fabricated to generate pressures of up to about 20 atmospheres without leakage or failure.

Referring to FIG. 16, the radiopaque markers 1620, 1622, 1624, and 1626 are all of the non-expandable type and are affixed to catheter or balloon tubing using adhesive, compression fit, interference fit, potting, over-molding, or the like. The radiopaque markers 1620, 1622, 1624, and 1626 are fabricated as short, axially elongate hollow cylinders using materials such as, but not limited to, platinum, gold, tantalum, iridium, barium, bismuth, or the like. The distal tip radiopaque marker 1620 can be affixed over, or distal to, the balloon bond 1608 for ease of assembly and can be generally covered by a distal shroud or fairing (not shown). The radiopaque markers 1622, 1624 and 1626 are affixed to the inner tubing 1610 prior to attachment of the dilator balloon 1604. The radiopaque marker 1622 delineates the approximate distal end of the full diameter region of the dilatation balloon 1604. The radiopaque marker 1626 delineates the approximate proximal end of the full diameter region of the dilatation balloon 1604. The marker 1626 can also be positioned to correspond to the proximal end of the fully expandable portion of the sheath (not shown). The marker 1624 can be generally optional and corresponds with the approximate center of the balloon 1604 or the expandable portion of the sheath (not shown). The inclusion of the radiopaque markers 1622, 1624, 1626 facilitates fluoroscopic visualization of the expandable portion of the sheath (not shown) or the dilatation balloon 1604 across the atrial septum to ensure correct positioning during sheath expansion. The distal marker 1620 facilitates fluoroscopic visualization of the distal tip of the dilator 1600 to ensure that it does not impinge on, perforate, or damage cardiac or other tissue structures within the body and that it follows the desired path within the patient. The distal dilator RO marker 1620 can be the most important of the RO markers in that it can be used to guide Brockenbrough needle advance and retraction during deployment of the system. In an embodiment, the filler tube 1628 can be used to surround the outer dilator tube 1612 to fill the dead space between the outer dilator tube 1612 and the inside of the sheath through which the dilator 1600 can be inserted. In an embodiment, the filler tube 1628 can be welded or bonded to the outer dilator tube 1612 at the distal filler bond 1630. The dilator sleeve, or filler tube 1628, can be fabricated from the same materials, including Hytrel, PEBAX, polyurethane, PVC, and the like, as those used for the outer dilator tube 1612. The filler tube 1628 provides a sheath system that can be more pushable and has increased resistance to kinking than would exist if the filler tube 1628 were omitted and a greater annular distance existed between the dilator outer tube 1612 and the sheath tubing (not shown).

FIG. 17A illustrates a radially expandable sheath system 1700, shown in its radially compressed configuration, comprising a dilator 1600 and an expandable trans-septal sheath 1400. The sheath 1400 further comprises a proximal anchor 1506, a distal anchor 1508, a sheath radiopaque marker 1702, a chevron transition zone 1704, and a fold line 1714. The dilator 1600 further comprises a dilatation balloon 1604, an inner dilation tube 1610, a distal tip radiopaque marker 1710, and a penetrator 1302. The penetrator 1302 is shown extended beyond the distal end of the inner dilator tubing 1610. The penetrator 1302, which can be a separate Brockenbrough needle or an integral device, is visible on fluoroscopy and the tip can be maintained proximally to the tip radiopaque marker 1710, which can be also visible under fluoroscopy, prior to advancing the penetrator 1302 to pierce the atrial septum. The distal tip radiopaque marker 1710 can be a ring or band of tantalum, platinum, iridium, gold, or the like. The thickness of the marker 1710 can range from 0.002 inches to 0.025 inches and preferably from 0.005 to 0.015 inches to ensure good visibility on the fluoroscope. The distal dilator RO marker 1710 can be affixed to the dilator tubing 1610 by processes such as, but not limited to, adhesives, bonding, welding, overmolding, or the like. The distal dilator RO marker 1710 can be preferably affixed near the distal end of the dilator tubing 1610 and can be spaced from 0.005 inches to 0.5 inches, and preferably between 0.010 and 0.25 inches from the distal end of the dilator tubing 1610. When the penetrator 1302 is advanced distally beyond the distal RO marker 1710, the penetrator can be substantially exposed and capable of punching through tissue. The distal RO marker 1710 can be covered by a distal tip fairing, nose cone, or other sleeve. The dilator 1600 comprises the dilator hub 1320 (FIG. 13), which can be affixed to the dilator shaft 1302. The dilator hub 1320, in an embodiment, further comprises anti-rotation elements (not shown) to prevent it from rotating relative to the sheath hub 1406 (FIG. 14). In an embodiment, such anti-rotation elements can include tabs on the dilator hub 1320 and slots on the sheath hub 1406, or visa versa, which can disengage by simple axial retraction of the dilator hub 1320 proximally away from the sheath hub 1406. The anti-rotation elements can prevent inadvertent distortion of the sheath system 1700 during insertion and manipulation inside the patient. The dilator 1600 can further comprise a fairing or distal shroud (not shown) that prevents the distal edge of the folded sheath tubing 1404 from catching on tissue as it can be being advanced distally. This distal shroud serves as a shoehorn to ensure that the sheath 1400-dilator 1600 combination 1700 can be smoothly advanced through a tissue puncture or endovascular lumen without becoming caught or hung up. The distal shroud can be preferably elastomeric to expand with the dilatation balloon 1604 and can be affixed at its distal end to the dilatation balloon 1604 or inner dilator tubing 1610, or both. The distal shroud retracts distally away from the expandable distal section 1404 of the sheath 1400 because it can be affixed to the dilator 1600.

FIG. 17B illustrates the sheath system 1700 in its radially, or diametrically, expanded configuration. The sheath system 1700 comprises the dilator 1600 and the sheath 1400. Also shown in FIG. 17B are the chevron transition zone 1704, the proximal balloon anchor 1506, the distal balloon anchor 1508, the anchor inflation line 1332, the steering linkage lumen 1424, and the sheath radiopaque marker 1702. The dilatation balloon 1604 is shown in its expanded, inflated configuration over the inner dilator tubing 1610. When the dilator balloon 1604 is deflated, the distal shroud (not shown) collapses diametrically and can be easily pulled proximally through the expanded tubing 1404 as the dilator 1600 is being withdrawn. The distal dilator RO marker 1710 is shown affixed to the dilator inner tubing 1610. The penetrator is not visible in this Figure and so can be retracted proximally to the distal dilator radiopaque marker 1710. By using the distal dilator RO marker 1710, it is possible to remove at least one step from the procedure. Typically the length of Brockenbrough needle protrusion beyond the distal end of the dilator can be correlated with the distance between the sheath hub and the Brockenbrough needle hub. This can be accomplished by inserting the Brockenbrough needle inside the sheath and measuring the distance between the dilator hub and the Brockenbrough needle hub with the Brockenbrough needle tip just proximal to the distal end of the sheath. This measurement step can be avoided as long as the physician is instructed not to allow the Brockenbrough needle to pass distally to the dilator distal RO marker prior to performing any punching procedural steps.

FIG. 17C illustrates the sheath 1400 after removal of the dilator 1600 (FIGS. 17A and 17B). The sheath 1400 further comprises the sheath hub 1406, the lever 1420, the proximal tubing 1402, the distal tubing 1404, the proximal anchor 1506, the distal anchor 1508, the sheath radiopaque marker 1702, and the transition zone 1704. The sheath 1400 can be fully expanded at its distal end 1404 and the proximal and distal anchors 1506 and 1508 are deflated. The proximal tubing 1402, the distal tubing 1404, or both can be fabricated using composite construction comprising a lubricious inner layer, a reinforcing layer, and an outer lubricious layer. Suitable materials for use in fabricating the inner layer and the outer layer include, but are not limited to, polyurethane, polyethylene, polypropylene, Hytrel, PEBAX, polyamide, and the like. Wall thicknesses of these layers can range from 0.0005 to 0.025 inches and preferably between 0.001 and 0.010 inches. In another embodiment, an elastomeric layer can be disposed outside the reinforcing layer and under the outer layer. In yet another embodiment, an elastomeric layer can be disposed between the reinforcing layer and the inner lubricious layer. The elastomeric layer can be fabricated from materials such as, but not limited to, thermoplastic elastomer, silicone elastomer, polyurethane elastomer, C-Flex, or the like. The proximal tubing 1402 in another embodiment, can be configured with a plurality of lumens to control the motion of multiple catheters that can be inserted therethrough. In an exemplary embodiment, the proximal tubing 1402 comprises two lumens that can each accept an 8 French catheter, or smaller, inserted therethrough. The lumens can be discreet or the separator wall can be removed at least in part to minimize catheter size. In the multiple lumen embodiment of the proximal region, the dilator 1600 can be inserted through one of the lumens. The cross-sectional shape of the proximal tubing 1402 can further be configured as non-circular to minimize the cross-sectional area while two round catheters, such as EP ablation or diagnostic catheters, are inserted therethrough. The distal region 1404 can be similarly ovalized or non-round but, because of its malleable nature, the distal region 1404 can be made capable of simply deforming to accept the two or more catheters. The sheath hub 1406 can further be configured with dual hemostasis valves and further include "Y" guides to facilitate placement of dual (or more) catheters therethrough.

Figure 18A:
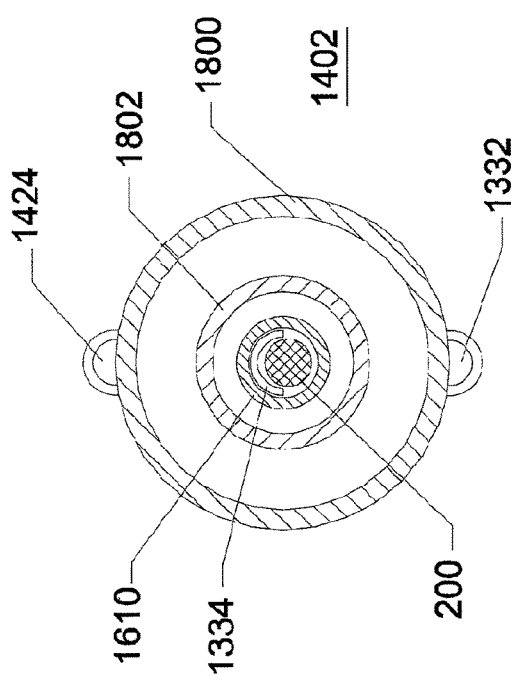
FIG. 18A illustrates a lateral cross-section of the proximal region of the expandable trans-septal sheath, according to an embodiment of the invention.

FIG. 18A illustrates a cross-sectional view of the sheath proximal end 1402. The proximal region 1402 further comprises the sheath tubing 1800, the outer dilator tubing 1802, the inner dilator tubing 1610, the guidewire 200, the penetrator linkage 1334, the steering linkage lumen 1424, and the anchor inflation lumen 1332. The sheath tubing 1800 can be, in an embodiment, a composite tube with an inner layer of lubricious material, an outer layer, and an intermediate reinforcing layer fabricated from a coil or braid. The coil or braid in the proximal region 1402 possesses spring characteristics and can be fabricated from stainless steel, titanium, nitinol, cobalt-nickel alloys, or the like. The coil or braid can also be fabricated from polymers such as PET, PEN, polyamide, HDPE, or the like. In an exemplary embodiment, the reinforcing layer can be a braid of PEN. The coil configuration can be fabricated from flat wire or from round wire. The coil or braid can be coated with radiopaque materials such as gold, tantalum, platinum, or the like, to enhance radiopacity. More than one steering linkage lumen 1424 can be used to achieve push-pull action, if separated by 180 degrees, or two-axis steering if separated by 90 degrees, or 120 degrees, for example.

Figure 18B:
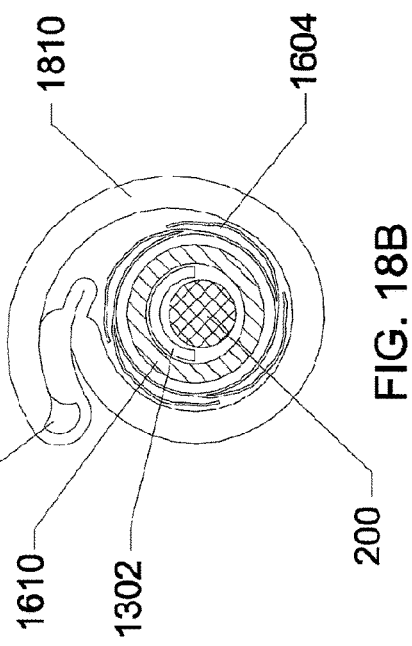
FIG. 18B illustrates a lateral cross-section of the distal region of the expandable trans-septal sheath in its non-expanded configuration, according to an embodiment of the invention.

FIG. 18B illustrates a cross-sectional view of the sheath distal region 1404 in its collapsed configuration. The sheath 1404 further comprises the distal expandable tubing 1810, the collapsed dilatation balloon 1604, the anchor inflation lumen 1332, the guidewire 200, the penetrator 1302, the inner dilator tube 1610, one or more longitudinal folds 1714, and the steering linkage lumen 1424. The distal expandable tubing 1810 can be, in an embodiment, a composite structure with an inner layer, an outer layer, both of which are formed from polymers similar to those used in the proximal region 1402, and an intermediate malleable reinforcing layer, preferably fabricated from annealed metals such as, stainless steel, gold, platinum, tantalum, or the like. In an exemplary embodiment, the malleable reinforcement comprises a coil of stainless steel 304, which has been substantially annealed. The stainless steel can be formed into a flat wire with a thickness of 0.002 to 0.004 inches and a width of 0.010 to 0.040 inches. The flat wire can be formed into a coil with a spacing substantially the same as the width of the flat wire. The stainless steel wire can be coated with a layer of gold to a thickness of 100 angstroms or more.

Figure 19:
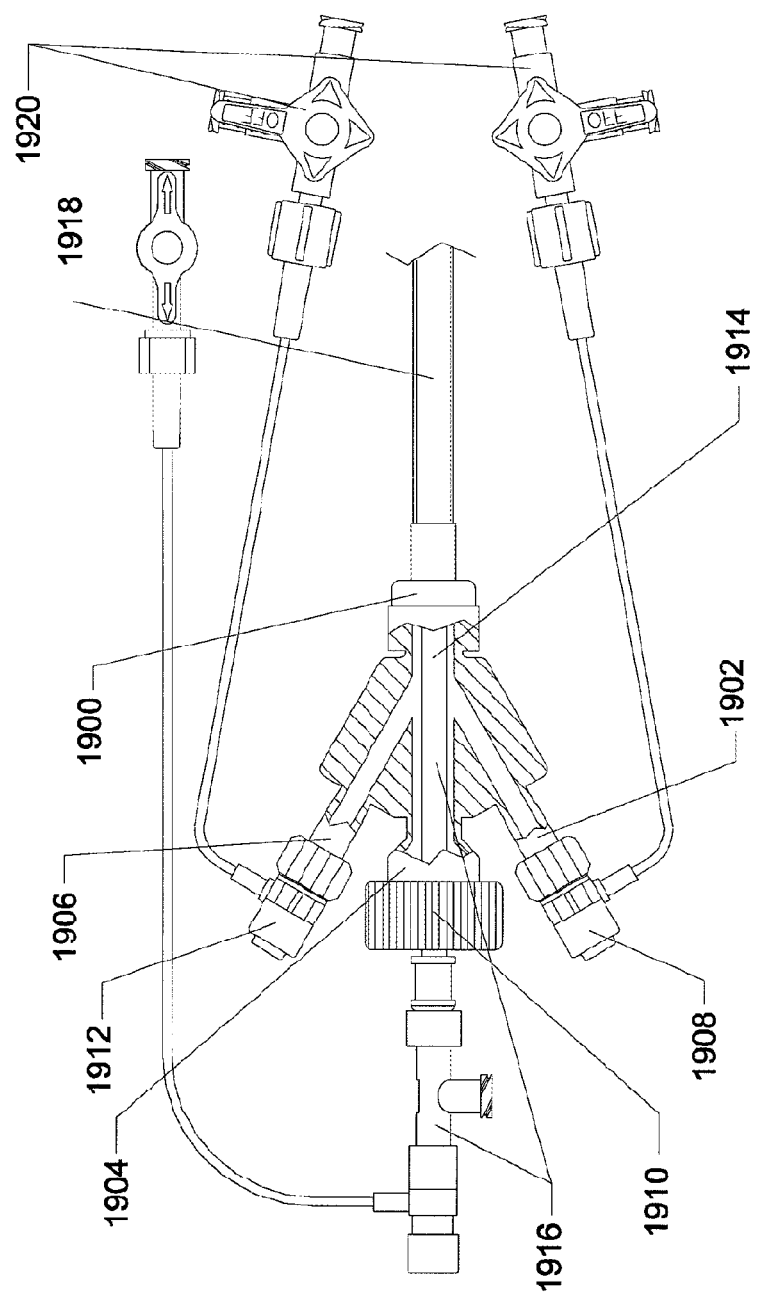
FIG. 19 illustrates a side view of a trans-septal sheath comprising multiple instrumentation ports on its hub, according to an embodiment of the invention.

FIG. 19 illustrates a side view of a trans-septal sheath triple-port hub 1900 comprising multiple instrumentation ports 1902, 1904, and 1906. The triple-port hub 1900 is shown in partial breakaway so that the internal lumen 1914 is visible. In the illustrated embodiment, the instrumentation ports 1902, 1904, and 1906 are affixed to the hub 1900. The instrumentation ports 1902, 1904, and 1906 further comprise hemostasis valves 1908, 1910, and 1912, which are operably connected to the communicating lumens of the instrumentation ports 1902, 1904, and 1906, which are, in turn, operably connected to the main through lumen 1914 of the hub 1900. The hemostasis valves 1908, 1910, and 1912 can be of the type, including but not limited to, ring gaskets, Tuohy-Borst valves, duckbill valves, stopcocks, ball valves, a combination thereof, or the like. The sheath dilator 1916 is shown slidably inserted into the sheath hub 1900 through the central hemostasis valve 1910, which can be a Tuohy-Borst valve in the illustrated embodiment. The Tuohy-Borst valve 1910 can be releasably tightened to restrain the position of the sheath dilator 1916 from moving in the axial direction. An advantage of the triple port hub 1900 over a two port hub can be that it can accommodate the dilator 1916 through the central port 1904 and a catheter each inserted through the sideports 1902 and 1904. The central port 1904 can be larger in diameter than the two sideports 1902 and 1906 and the central port 1904 can accommodate very large catheters up to 10 to 30 French in diameter. The Tuohy-Borst valve 1910 can be configured to permit sealing around these large catheters and can optionally close completely or partially. The partial closure Tuohy-Borst valve requires a hemostasis adapter (not shown) in order to plug the partial opening and prevent loss of hemostasis or ingress of air.

The dilator 1916 can be withdrawn from the hub 1900 following inflation of the expandable part of the sheath (not shown) and deflation of the balloon (not shown) on the dilator 1916. The dilator 1916 generally requires a larger port than that used for catheterization so the central port 1904 can be configured for this task. The side ports 1902 and 1906 have lumens that can accommodate catheters in the approximate range of 4 to 10 French or larger in diameter.

FIG. 20A illustrates a side view of the distal end 2000 of another embodiment of trans-septal sheath and dilator comprising curvature near its distal end to facilitate trans-septal puncture. In this embodiment, the distal end 2000 comprises a transition zone 2002, an expandable distal region 2004, a distal tapered fairing 2006, a stylet 2008, and a proximal zone 2010 further comprising an outer layer 2014, an intermediate reinforcing layer 2012, and an inner layer 2016. The distal end 2000 also comprises a flexible zone 2026 further comprising an outer layer 2018, an intermediate reinforcing layer 2022, an inner layer 2024, a plurality of vent holes 2028, and a flexible intermediate layer 2020. The tapered distal fairing 2006 further comprises at least one pressure relief vent 2030. The tapered distal fairing 2006 and the distal most part of the expandable region 2004 can comprise a lubricious outer coating 2032.

Referring to FIG. 20A, the flexible zone 2026 can be disposed proximal to the expandable distal region 2004 and can be affixed thereto by the transition zone 2002. The flexible zone 2026 can be affixed to and disposed distal to the proximal zone 2010. The flexible zone 2026 can be characterized by the flexible intermediate layer 2020. The flexible intermediate layer 2020 can be comprised of elastomeric materials including, but not limited to, thermoplastic elastomer, silicone elastomer, polyurethane elastomer, polyester elastomer, or the like. An exemplary thermoplastic elastomer can be commercially available under the name of C-Flex. The flexible intermediate layer 2020 can have a sticky or tacky surface which may be unsuitable for body or blood contact. For this reason, the flexible intermediate layer 2020 can be preferably sandwiched between the inner layer 2024 and the outer layer 2018, both of which can be fabricated from lubricious materials such as, but not limited to, high durometer polyurethane, polyethylene, polypropylene, polytetrafluoroethylene, polyamide, or the like. The flexible zone 2026 can advantageously increase the flexibility of a sheath, especially a large diameter sheath in selected regions. This increased flexibility can be beneficial when the sheath requires steering by a device such as a Brockenbrough needle or when a large diameter sheath with specific strength characteristics must follow a guidewire. The reinforcing layer 2022 can be embedded within the flexible intermediate layer 2020 or it can reside either inside or outside the flexible intermediate layer 2020. The flexible intermediate layer 2020 can reside only in the flexible region 2026 or it can extend partially or fully across the transition zone 2002 and partially or completely extend to the distal end of the expandable region 2004. In the illustrated embodiment, the reinforcing layer 2022 can be a braided tubular structure and can be fabricated from material such as, but not limited to, PEN, PET, stainless steel, titanium, nitinol, or the like. The braided reinforcing layer 2022 can be suitable for torque transmission and longitudinal pushability as well as kink resistance. This braided reinforcing layer 2022 can be the same material and structure as that used for the proximal reinforcing layer 2012 or it can have a different structure or material makeup.

The stylet 2008 can be a packaging aid fabricated, for example, from spring stainless steel, titanium, or the like. The stylet 2008 can be formed straight or formed with a curve such as shown in FIG. 20A. The curved stylet 2008 can help maintain the distal end 2000 in a curved configuration prior to use by the physician. The stylet 2008 can be a circular mandrel that can be slidably engaged within the central lumen of the sheath dilator. The diameter of the stylet 2008 can range between approximately 50% and 95% of the dilator central lumen and in an embodiment, can range in size between approximately 0.035 and 0.050 for a dilator central lumen configured to accept a Brockenbrough needle. The stylet 2008 can have a length of 1 cm to 100 cm and preferably range between 5 cm and 50 cm. The vent holes 2028 perforate completely through the sheath wall and operably connect the inner sheath lumen to the environment outside the sheath. The vent holes 2028 can be used for flushing and aspiration of the sheath prior to being inserted within the patient. The flushing can be generally performed using a syringe (not shown) filled with heparinized saline. Referring to FIG. 19, the syringe can be operably connected to one or all of the sheath sideport stopcocks 1920 which are affixed to the purge lead lines 1922. The heparinized saline can be injected into the stopcocks 1920 and flows into the central lumen of the sheath 1914 where it can flow to the distal end of the sheath, displacing air as it moves, and exit at the vent holes 2028, which are disposed proximate the distal end of the sheath, either proximate the transition zone 2002 or the expandable region 2004. It can be advantageous or important to remove air from the system prior to use so that air is not entrained into the patient's cardiovascular system during use, an event that could lead to ischemic sequelae. Aspiration can also be performed through the vent holes 2028 by withdrawing a vacuum on the stopcock and withdrawing blood into the vent holes 2028, again to displace air.

The pressure relief vent 2030 can be a hole or slit in the distal fairing 2006 that operably communicates with the underside of the distal fairing 2006. Fluid injected into the central lumen of the sheath can find its way under the distal fairing 2006 and a buildup of pressure under the distal fairing 2006 can be relieved by the pressure relief vent 2030. The distal fairing 2006 and a portion of the expandable region 2004 can be coated with a thin layer of hydrophilic lubricious coating 2032. The lubricious coating 2032 advantageously extends only partially or completely to approximately the transition zone 2002. Grasping the distal end of the sheath can be important during insertion and the lubricious coating 2032 should not extend to the region where the sheath can be grasped or the grip will be compromised. In an embodiment, the distal most 2 to 3 cm of expandable region 2004 can be coated along with the fairing tip 2006.

Typical lubricious coatings 2032 can be polyurethane based and can be adhered to the sheath outer surface by mechanical or chemical bonding. Other coatings 2032 can include heparin or other anticoagulants or antimicrobial agents.

The transition zone 2002 can be a simple butt joint between the material of the expandable region 2004 and the flexible region 2026. In another embodiment, illustrated in FIG. 20, the transition zone 2002 can comprise chevrons 2034 or interdigitating fingers of material to provide for a gradual transition of material properties with in the transition zone. In one embodiment, the built-up construction of the flexible region 2026 can be the same as that within the expandable region 2004 with the exception that the reinforcing layer 2022 in the flexible zone can be preferably elastomeric and braided, while the reinforcing layer (not shown) in the expandable region 2004 can be preferably highly malleable. The reinforcing layer (not shown) in the expandable region 2004 can be a coil of flat wire, or it can be a braid, stent-shape, or other structure. In an embodiment, only the reinforcing layer changes across the transition zone 2002 and in this embodiment, the non-chevron configuration can be more appropriate. The curve shown in the distal end of the sheath 2000 can either be passive and supported by the stylet, or it can be heat-set in place during manufacturing. In the illustrated embodiment, the primary curve can be in the flexible region 2026 and it can be desirable to use materials in the flexible region 2026 that can retain their shape once set. Such materials include, but are not limited to polyethylene, PTFE, Hytrel, C-Flex, PEBAX, and the like.

FIG. 20B illustrates a side view of the distal end of the sheath comprising the expandable tubing 2004 further comprising a distal end 2044, the tapered distal fairing 2006, the dilator tubing 2038, a distal radiopaque marker 2034, the pressure relief port 2030, and a fairing fastener 2040 further comprising a fairing fastener to tubing bond 2042. The tapered distal fairing 2006 further comprises the reverse taper 2036 at its proximal end. The reverse taper 2036 thins out the fairing near the proximal end so that it can flex and follow the expandable tubing 2004 as it can be routed into the patient. The tapered distal fairing 2006 can be shown covering the distal end 2044 of the expandable region 2004. In another embodiment the tapered distal fairing 2006 can butt up against, but not cover, the distal end 2044 of the expandable region 2004. The fairing fastener 2040 can be affixed to the dilator tubing 2038 near the distal end by the bond 2042, said bond 2042 being formed by welding, melting, adhesive bonding, mechanical interlock, or the like. The fairing fastener 2040 can be fabricated from the same or similar materials as the dilator tubing 2038 to ensure an optimal attachment. In an embodiment, the fairing fastener 2040 can be embedded within the distal fairing 2006. In an embodiment of the manufacturing process to form the bond 2042, the distal fairing 2006 can be placed over the dilator tubing 2038. The fairing fastener 2040 can be placed over the dilator tubing 2038 distal to the distal fairing and can be moved so that its proximal end extends over the outside of the distal fairing 2006. A length of shrink wrap can be placed around the fairing fastener 2040 and distal fairing 2006. Heat can be applied to the shrink wrap which reduces in diameter and generates radially inward pressure on the fairing fastener 2040. In combination with the heat, which melts the distal fairing 2006, and welds the fairing fastener 2040 to the dilator tubing 2038, the force of radial compression causes the fairing fastener 2040 to become embedded within the distal fairing 2006 and the distal end of the fairing fastener 2040 bonds or becomes welded to the dilator tubing 2038. In an embodiment, the distal fairing 2006 can be fabricated from silicone elastomer, thermoplastic elastomer, Hytrel, or the like. In another embodiment, the distal fairing 2006 can be loaded with barium sulfate, tantalum powder, bismuth sulfate, or the like to improve radiopacity and allow for visibility of the distal fairing 2006 under fluoroscopy or X-ray. In an embodiment, the distal fairing 2006 can be injection molded, liquid injection molded, or cast.

A embodiment of the trans-septal sheath can be the procedure or method of use. An exemplary procedure begins by preparing the device as follows. A standard cardiac, trans-septal preparation should be completed per hospital protocol. Standard fluoroscopic equipment should be available for use during the procedure. Proper radiological protection should be provided for all attending personnel. Using aseptic technique, remove the sheath from its sterile pouch. Visually inspect the sheath to make sure there is no distortion or kinking in the shaft of the sheath or in the folded distal end and that a smooth taper exists between the distal end of the sheath and the balloon dilator. The balloon dilator shaft is clamped into position within the Sheath by the closed Tuohy-Borst valve on the proximal end of the Sheath. Use aseptic technique for all steps of the procedure. Open the three-way stopcock, located on the through-lumen flush port of the sheath, and flush with sterile, heparinized saline. Close the stopcock. Open the three-way stopcock on the sheath sideport flush port and flush with sterile, heparinized saline to ensure that all air is removed from the Sheath. Verify saline flow from the distal drain ports on the sheath. Close the stopcocks to prevent saline loss or air embolism during the procedure. Remove a Brockenbrough Needle from its package and remove the stylet from the Needle. With the stopcock in the open position, flush the Brockenbrough needle with heparinized saline. Reinsert the stylet and lock it onto the hub. Open the three-way stopcock on the Expander Flush Port and flush with sterile, heparinized saline to ensure that all air is removed from the Expander guidewire lumen. Open the Tuohy-Borst valve on the proximal end of the Expander Hub and verify saline flow out through the Tuohy-Borst valve. Close the stopcock and Tuohy-Borst valve. Loosen the Tuohy-Borst valve and fully insert the Brockenbrough needle into the Tuohy-Borst valve on the Expander. Advance the needle until it extends beyond the distal tip of the Expander. Withdraw the Brockenbrough needle until its tip is just within the distal end of the Expander. Measure the distance between the pointer flange on the proximal end of the Brockenbrough needle and the proximal end of the Tuohy-Borst valve on the Expander Hub.

Fully remove the Brockenbrough needle from the sheath dilator assembly, open the 3-way stopcock, and again flush through the dilator flush port, using heparinized saline, making sure fluid flows from the distal end of the dilator. Attach the through lumen of a high pressure stopcock to a high pressure line attached to a pressure transducer for later connection to the Brockenbrough needle for intra-atrial blood pressure measurements. A Seldinger preparation and access are completed into the right femoral vein using, for example, an 18-gauge thin wall access hollow needle. A 0.038" stiff guidewire with a floppy tip is advanced through the access needle and into the femoral vein. Route the 0.038" guidewire into the venous system, through the inferior vena cava, and into the superior vena cava under fluoroscopic guidance.

Ensure that all hemostasis valves and Tuohy-Borst valves are closed and that all ports have been flushed and primed with heparinized saline and are free of air. The sheath with its integral balloon dilator is advanced as a single unit, under fluoroscopic control, over the 0.038" guidewire until its tip radiopaque marker is positioned well within the superior vena cava. Inject radiopaque contrast media through the dilator flush port, as required, under fluoroscopic visualization to ensure correct placement. Carefully controlling the hemostasis valve at the proximal end of the dilator hub, remove the guidewire. Carefully attach a 10-cc syringe filled with 1-cc of sterile heparinized saline to the dilator flush port and withdraw until blood is observed. Repeat this procedure to ensure the dilator flush port is free of air. Insert the Brockenbrough needle with stylet into the needle guidewire port of the dilator and route the Brockenbrough needle so that its tip is aligned behind (proximal to) the radiopaque marker located at the distal tip of the sheath dilator. This is confirmed using the dimensions measured earlier between the pointer flange and the sheath proximal end. Rotate the Brockenbrough needle and sheath dilator so that the pointer on the Brockenbrough is aligned with the sheath hub sideport and that both Brockenbrough pointer and sheath hub Sideport are oriented medially. Remove the stylet from the Brockenbrough needle and attach the 3-way, high pressure stopcock with attached pressure transducer to the Luer port of the Brockenbrough needle. Attach a 10-cc syringe filled with 1-cc of heparinized, sterile saline to the side port of the 3-way stopcock. Withdraw blood into the 10-cc syringe. Close the 3-way stopcock and remove and discard the syringe. Repeat the blood withdrawal with another new 10 cc filled with 1 cc of heparin to ensure the absence of air.

The sheath dilator assembly, with Brockenbrough needle inserted, is withdrawn caudally with the tip of the Brockenbrough needle oriented medially, toward the atrial septum as evidence by the orientation of the pointer flange being at 3:00 to 5:00 as observed from the patient's feet. Withdrawal of the sheath dilator assembly will result in the tip moving medially when it enters the right atrium. When, upon further withdrawal, the tip of the sheath dilator assembly abruptly moves markedly medially into the fossa ovalis, further withdrawal is discontinued and the atrial septal wall should be engaged. The fossa ovalis is now "tented" toward the left atrium. Using a 10-cc syringe filled with radiopaque contrast media, inject a small amount of contrast media through the high pressure stopcock attached to the central lumen of the Brockenbrough needle to "paint" the fossa ovalis with a mark that is visible under fluoroscopy. Carefully monitoring the pressure within the lumen of the Brockenbrough needle, the Brockenbrough needle is next advanced out of the sheath dilator assembly and through the atrial septum into the left atrium, taking care not to move the sheath dilator assembly. Continuous fluoroscopic monitoring is essential during this phase. The fossa ovalis will, under mechanical pressure, move laterally over the sheath dilator assembly so that the distal end of the sheath dilator assembly now resides within the left atrium as indicated by pressure waveforms consistent with the left atrium and fluoroscopic observation. The proximal and distal sheath radiopaque markers (second and third RO markers from the distal end of the sheath dilator assembly) should now straddle the position of the fossa ovalis the location of which is evidenced by the "painted" mark generated in a prior step.

A dilute 50% solution of radiopaque contrast media, and sterile saline is prepared and approximately 25-CC are drawn up into a high-pressure balloon inflation syringe equipped with a pressure gauge. Care should be taken to remove all air from the syringe, the dilator, and associated tubing. Attach the pressure line of the inflation device to the through lumen of the 3-way stopcock attached to the dilator balloon inflation port. Attach a syringe, filled with radiopaque contrast media, to the other lumen of the three-way stopcock. Under fluoroscopic control, the dilute contrast media is injected up to the maximum rated inflation pressure. It is normal to observe a drop in pressure as the dilator balloon progressively expands the folded distal section of the sheath. The rated inflation pressure should be maintained for a minimum of 30 seconds to expand any "waist" that may remain along the length of the expanded sheath.

Apply suction, using the high-pressure syringe, to the inflation/deflation port attached to the 3-way stopcock on the balloon dilator hub in order to deflate the balloon of the dilator. Slightly loosen the Tuohy-Borst valve on the through lumen at the proximal end of the sheath hub. Remove the deflated dilator from the expanded sheath being careful to immediately close the Tuohy-Borst valve to prevent blood loss. Introduce the appropriate therapeutic or diagnostic catheter through the central working channel of the expanded sheath into the left atrium. A 9 French hemostasis adaptor (provided) may be inserted and sealed within the Tuohy-Borst valve to facilitate introduction and removal of diagnostic or therapeutic devices. This adaptor may be placed after the dilator has been removed from the Tuohy-Borst valve. Before placement, flush the adaptor with heparinized saline to remove air. Insert the stem of the hemostasis adaptor into the Tuohy-Borst valve and tighten snugly by hand. When the hemostasis adaptor is secured, connect a 10 cc syringe filled with 1 cc of heparin to the adaptor sidearm stopcock and withdraw blood to ensure the absence of air in the system. The hemostasis adapter is now ready for use. Remove any instrumentation from the sheath, being careful to control the Tuohy-Borst or hemostasis valves to prevent blood loss. While maintaining hemostasis and using standard hospital procedure to control a venous percutaneous puncture site, gently withdraw and remove the expanded sheath from the venous circulation when the procedure has been completed.

FIG. 21A illustrates a side view of a hemostasis adapter 2100 comprising an adapter hub 2102, a length of adapter tubing 2104, a hemostasis valve 2106, a sideport 2114 further comprising a purge line 2108 and a stopcock 2110, and a tubing enlargement 2112. The tubing enlargement 2112 can be a cylindrical or radially enlarged structure, bonded, welded, or mechanically affixed to the adapter tubing 2104. The hub 2102 can be affixed to the proximal end of the adapter tubing 2104. The adapter tubing 2104 comprises a central through lumen 2116 extending from the proximal end to the distal end of the adapter tubing 2104. The sideport 2114 can be affixed to the hub 2102 and operably connected to the central through lumen 2116. The purge line 2108 can be affixed to the sideport 2114 at one end and to the stopcock 2110 at the other end. The hemostasis valve 2106 can be a ring orifice, duckbill valve, flap valve, or a combination thereof. In a preferred embodiment, the hemostasis valve 2106 comprises a proximal ring seal and a distal flap valve to optimize the valving function. The enlargement 2112 can be configured to serve as a tactile stop or detent so that an operator can feel how far to insert the hemostasis adapter tubing 2104 into a hub of another sheath (not shown). The enlargement 2112 can be advantageously beveled or tapered at one or both ends to facilitate passage through larger valves or ports. The adapter tubing 2116 can also be beveled at its distal end to facilitate passage through another tube or valve (not shown).

FIG. 21B illustrates the hemostasis adapter 2100 inserted through the Tuohy-Borst valve 1910 on the central through port of a sheath hub 1900. The sheath hub 1900 comprises a large diameter Tuohy-Borst valve 1910, which can have a capacity ranging from 10 to 30 French. Such large Tuohy-Borst valves 1910 may not seal fully on closure, or it may seal at all unless it surrounds a tube larger than 5 or 6 French, for example. The hemostasis adapter 2100 can be inserted into such a Tuohy-Borst valve 1910 and the Tuohy-Borst valve 1910 tightened to obtain a seal around the hemostasis adapter tubing 2104, which can range in diameter from 5 to 10 French. In an embodiment, the Tuohy-Borst valve 1910 can seal around and allow passage of tubing ranging from 6 to 18 French in diameter. The enlargement 2112 can pass through the Tuohy-Borst or other valve 1910 but with increased force, which can be relieved once the enlargement 2112 can be past the valve 1910. The enlargement 2112 also helps prevent inadvertent withdrawal of the hemostasis adapter 2100 from the sheath hub 1900. The stopcock 2110 and purge line 2108 can be used for aspiration of blood or saline or purging of air from the adapter lumen 2116 or the sheath lumen 1914.

FIG. 22A illustrates a side view of the distal end 2200 of an expandable trans-septal sheath with the dilator removed. The distal end 2200 can be shown in partial breakaway view so the reinforcing structures 2208 and 2210 can be visualized. The distal end 2200 comprises a proximal reinforcement 2208, a sheath distal tubing wall 2204, a central sheath lumen 2214, a distal reinforcement 2210, a distal radiopaque marker 2212, and a transition zone 2206. In an embodiment, the distal reinforcement 2210 can be a flat wire fabricated from annealed stainless steel. In another embodiment, the distal reinforcement can be a flat wire fabricated from annealed stainless steel that has been coated with a radiopaque coating such as, but not limited to, gold, platinum, iridium, tantalum, or the like. The coating can be in the range of 50 to 300 angstroms to maximize visibility under fluoroscopy. The radiopacity-enhanced distal reinforcement 2210, in the illustrated embodiment can be in the shape of a coil but could be another structure like a zigzag shape. The distal radiopaque marker 2212 delineates the distal end of the sheath tubing 2200. In the illustrated embodiment, the proximal reinforcement 2208 can be a braided structure fabricated from spring wire or elastomeric polymer. The proximal end of the transition zone 2206 can be where the proximal reinforcement 2208 ends. The distal reinforcement 2210 can be affixed to the sheath wall 2204 by first placing an inner polymer layer, fabricated from polyethylene for example, over a mandrel, followed by the reinforcing coil 2210. An outer layer can be then placed over the reinforcing coil 2210 and the entire structure can be heated under pressure by using shrink wrap, for example PET or PTFE, to provide radially directed inward force to fuse the structure given the applied heat.

FIG. 22B illustrates a side view of the distal end 2220 of an expandable trans-septal sheath with the dilator removed. The distal 2200 end of the sheath is shown in partial breakaway view so that the reinforcement can be visualized. The distal end 2200 comprises the transition zone 2206, the sheath wall 2204, the distal reinforcement 2210, the distal radiopaque marker 2212, and a parallel wound coil of radiopaque wire 2222. The transition zone 2206 can comprise a chevron shape with interdigitating fingers, as illustrated, or it can be a simple flat butt joint. The parallel wound coil 2222 can be preferably fabricated from gold, platinum, tantalum, iridium, or the like. The parallel wound coil 2222 and the distal reinforcement 2210 are affixed to the sheath wall 2204 by first placing an inner layer over a mandrel, followed by the reinforcing coil 2210 and the parallel wound coil 2222. An outer layer can be then placed over the coils and the entire structure can be heated under pressure by using shrink wrap to provide radially directed inward force to fuse the structure.

By varying the length of the expandable region, different properties can be achieved. A short expandable region allows for a stiffer catheter with highly controllable characteristics, wherein curves can be heat set into the structure more readily. A longer expandable region allows the sheath dilator system to be bent and articulated by a guidewire or Brockenbrough needle, inserted through the central lumen of the dilator. In an embodiment, the expandable region can be approximately 10 to 30 cm long and preferably between 15 and 25 cm long. In another embodiment, the expandable region can be between 1 and 10 cm long and preferably between 2 and 5 cm long. In the embodiment where the expandable length can be short, an enhanced flexible region can be used as part of the catheter to improve flexibility, even when the sheath can be a large diameter structure. In either embodiment, it can be beneficial that the Brockenbrough needle be able to steer the sheath dilator system to point toward the fossa ovalis.

The present invention may be embodied in other specific forms without departing from its spirit or essential characteristics. For example, the sheath may include instruments affixed integrally to the interior central lumen of the sheath, rather than being separately inserted, for performing therapeutic or diagnostic functions. The hub may comprise tie downs or configuration changes to permit attaching the hub to the mouth, nose, or face of the patient. The dilatation means may be a balloon dilator as described in detail herein, it may rely on axial compression of a braid to expand its diameter, or it may be a translation dilator wherein an inner tube is advanced longitudinally to expand an elastomeric small diameter tube. Dilation may also occur as a result of unfurling a thin-film wrapped tube or by rotation of a series of hoops so that their alignment is at right angles to the long axis of the sheath. The embodiments described herein further are suitable for fabricating very small diameter catheters, microcatheters, or sheaths suitable for cardiovascular or neurovascular access. Various valve configurations and radiopaque marker configurations are appropriate for use in this device. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A method of instrumenting the left atrium comprising the steps of:
   routing a guidewire into the right atrium from a peripheral vein;
   inserting a sheath into the patient over the guidewire; the sheath having a pre-inserted dilator, a hub affixed to a proximal end of the sheath, and a hemostasis adapter having an adapter tubing with an enlargement that both pass through a valve of the hub; said enlargement having a cylindrical shape and being beveled at a proximal end to a surface of the adapter tubing and beveled at a distal end of said enlargement to the surface of the adapter tubing;
   advancing the sheath to a treatment or diagnostic site within the right atrium of the heart, wherein the sheath comprises a distal region which is collapsed in diameter;
   performing a trans-septal puncture between the right and left atrium and advancing the collapsed sheath through the puncture into the left atrium;
   dilating the distal region of the sheath so that the distal region of the sheath is expanded, wherein a full-size lumen exists within the sheath and extending from the proximal end to the distal end;
   collapsing the dilator by an action applied at the proximal end of said dilator;
   removing the dilator from the sheath;
   inserting instrumentation through the lumen of the sheath into the left atrium;
   performing therapy or diagnosis with the instrumentation; and
   removing the sheath from the patient.

2. The method of claim 1 wherein the dilation step is performed by inflating a balloon on the dilator.

3. The method of claim 1 wherein the dilation step is performed by attaching a liquid-filled inflation device to a balloon inflation port at the distal end of the dilator and infusing liquid under pressure into the dilator.

4. The method of claim 1 wherein the step of collapsing the dilator comprises withdrawing a plunger on the inflation device to withdraw liquid from the dilator.

5. The method of claim 1 wherein the therapy comprises electrophysiology energy delivery.

6. The method of claim 1 wherein instrumentation comprises inserting two or more catheters through the sheath to perform the therapy.

7. The method of claim 1 wherein the therapy comprises delivering an implant into the left atrium.

8. The method of claim 1 wherein dilation of the sheath also comprises the step of dilating anchors within the atria.

9. The method of claim 1 wherein the full-size lumen created in the expandable region by the dilator is substantially larger than the lumen of the proximal non-expandable tubing.

10. The method of claim 1 wherein the full-size lumen created in the expandable region by the dilator is substantially smaller than that of the proximal sheath lumen.

11. The method of claim 1 wherein the full-size lumen created in the expandable region by the dilator is substantially the same size as that of the proximal sheath lumen.

12. The method of claim 1, further comprising the step of removing the guidewire and inserting a Brockenbrough needle through the central lumen of the sheath dilator.

13. The method of claim 1, further comprising the steps of advancing the guidewire, and subsequently the sheath, into the superior vena cava; removing the guidewire; inserting a Brockenbrough needle to just inside the distal end of the sheath dilator; and withdrawing the sheath, pre-inserted dilator, and Brockenbrough needle assembly retrograde into the right atrium.

* * * * *